(12) United States Patent
Weissman et al.

(10) Patent No.: US 7,261,741 B2
(45) Date of Patent: Aug. 28, 2007

(54) PROSTHESIS WITH RESORBABLE COLLAR

(75) Inventors: Marc G. Weissman, Warsaw, IN (US); J. Brock VanMeter, Leesburg, IN (US); Thomas S. Camino, Warsaw, IN (US); Thomas Thornhill, Dover, MA (US); Thomas Schmalzried, Rolling Hills, CA (US); Daniel Berry, Rochester, MN (US); John Callaghan, Iowa City, IA (US); David Fisher, Fisher, IN (US)

(73) Assignee: Depuy Products, Inc., Warsaw, IN (US)

( * ) Notice: Subject to any disclaimer, the term of this patent is extended or adjusted under 35 U.S.C. 154(b) by 170 days.

(21) Appl. No.: 10/155,618

(22) Filed: May 24, 2002

(65) Prior Publication Data

US 2003/0109933 A1 Jun. 12, 2003

Related U.S. Application Data

(60) Provisional application No. 60/302,113, filed on Jun. 30, 2001.

(51) Int. Cl.
*A61F 2/36* (2006.01)
(52) U.S. Cl. ............................... 623/23.22; 623/23.21; 128/898
(58) Field of Classification Search ................ 623/623, 623/23.21–23.23
See application file for complete search history.

(56) References Cited

U.S. PATENT DOCUMENTS

| | | | |
|---|---|---|---|
| 4,012,796 A | * | 3/1977 | Weisman et al. ........ 623/23.28 |
| 4,308,550 A | | 12/1981 | Forte |
| 4,770,660 A | | 9/1988 | Averill |
| 4,827,919 A | | 5/1989 | Barbarito et al. |
| 4,997,448 A | | 3/1991 | Filer |
| 5,171,275 A | | 12/1992 | Ling et al. |
| 5,171,289 A | * | 12/1992 | Tornier .................... 623/22.44 |
| 5,290,318 A | | 3/1994 | Ling et al. |
| 5,314,489 A | | 5/1994 | Hoffman et al. |
| 5,458,653 A | * | 10/1995 | Davidson ................. 623/23.36 |
| 5,733,338 A | | 3/1998 | Kampner |
| 5,766,262 A | | 6/1998 | Mikhail |
| 5,935,172 A | | 8/1999 | Ochoa et al. |
| 6,017,366 A | | 1/2000 | Berman |
| 6,017,975 A | | 1/2000 | Saum et al. |
| 6,214,049 B1 | | 4/2001 | Gayer et al. |
| 6,228,900 B1 | | 5/2001 | Shen et al. |
| 6,494,916 B1 | * | 12/2002 | Babalola et al. ............ 623/23.3 |

FOREIGN PATENT DOCUMENTS

| | | |
|---|---|---|
| EP | 0 295 360 B1 | 1/1988 |
| EP | 0 216 489 B1 | 8/1988 |
| EP | 1 201 205 A1 | 10/2001 |
| FR | 2 687 306 A1 | 2/1992 |
| WO | WO94/07439 A1 | 9/1993 |
| WO | WO97/06752 A1 | 11/1994 |
| WO | WO95/13757 A1 | 8/1996 |
| WO | WO97/40785 A1 | 3/1997 |

* cited by examiner

*Primary Examiner*—Thomas Barrett

(57) ABSTRACT

A articulating hemiarthroplasty prosthesis (10) for use in arthroplasty is provided. The prosthesis includes a stem (12) for implantation at least partially within the medullary canal (14) of a long bone (16) and a collar (20). The collar (20) is operably associated with the stem (12) and extends outwardly therefrom. At least a portion of the collar (20) includes a resorbable material. The prosthesis includes a head (30) and a cup (46) for engagement with the head (30).

3 Claims, 35 Drawing Sheets

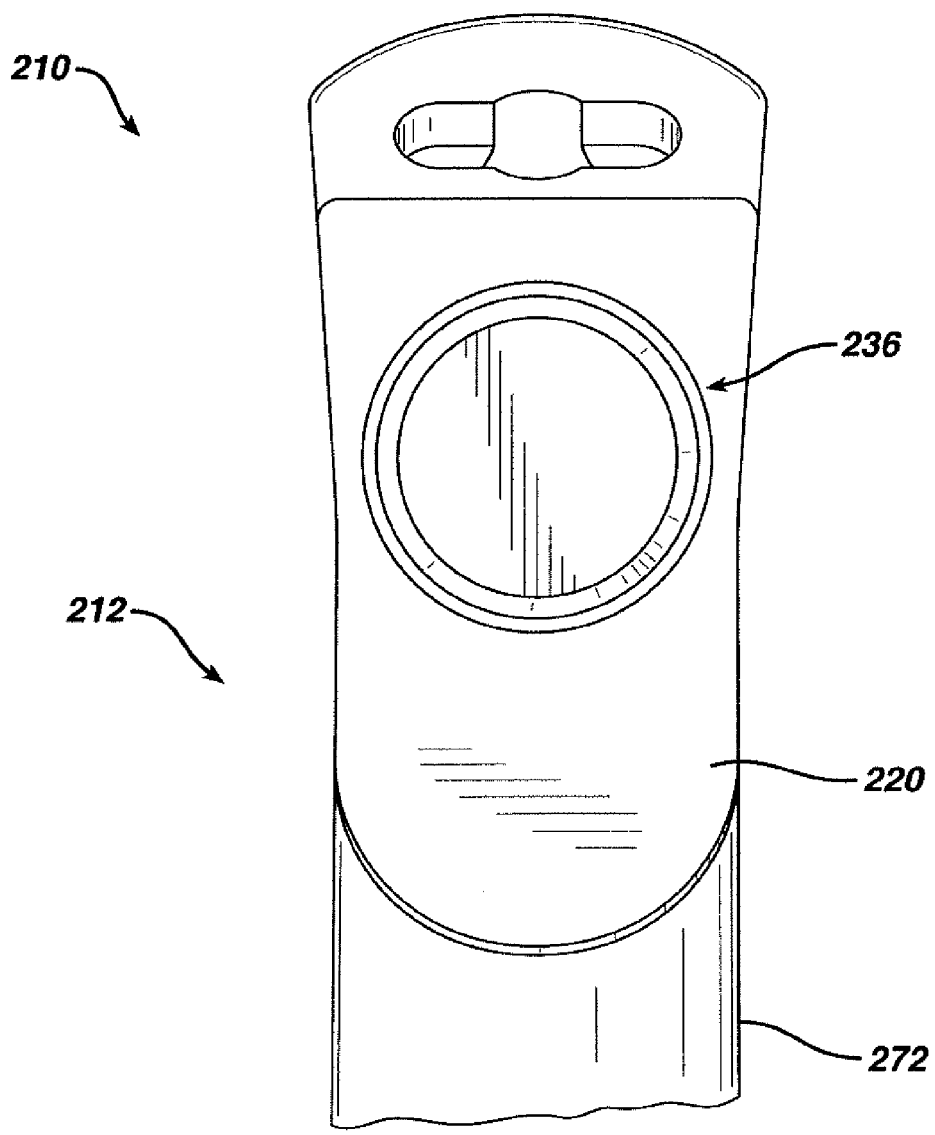

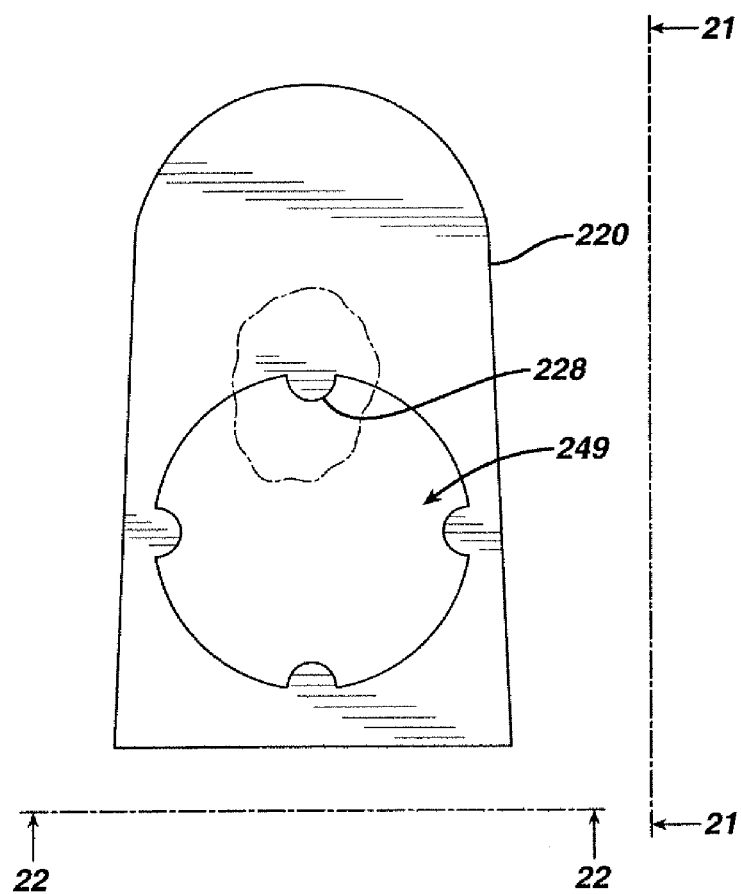
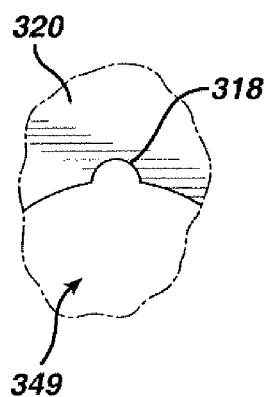
FIG. 20
FIG. 20A

PROSTHESIS WITH RESORBABLE COLLAR

CROSS REFERENCE TO U.S. PROVISIONAL PATENT APPLICATION

This application is a Utility Application based upon U.S. Provisional Patent Application Ser. No. 60/302,113 filed Jun. 30, 2001, entitled PROSTHESIS WITH RESORBABLE COLLAR.

TECHNICAL FIELD OF THE INVENTION

The present invention relates generally to the field of orthopaedics, and more particularly, to an implant for use in arthroplasty.

BACKGROUND OF THE INVENTION

This invention relates to implantable articles and methods for manufacturing such articles. More particularly, the invention relates to bone prosthesis and process for manufacturing the same.

There are known to exist many designs for and methods for manufacturing implantable articles, such as bone prostheses. Such bone prostheses include components of artificial joints, such as elbows, hips, knees and shoulders. An important consideration in the design and manufacture of virtually any implantable bone prosthesis is that the bone prosthesis has adequate fixation when implanted within the body.

Early designs of implantable articles have relied upon the use of cements such as polymethylmethacrylate (PMMA) to anchor the implant. The use of such cements can have some advantages, such as providing a fixation that does not develop free play or does not lead to erosion of the joining faces postoperatively. Maintaining a load or force at the cement bone interface assists in providing for good fixation and to prevent motion.

To assist in maintaining the load at the cement bone interface tapered, some highly polished stems have been designed without a proximal collar to permit the subsidence within the cement mantle. The stems are thus permitted to move distally with respect to the resected bone. Long term controlled subsidence within the cement mantle minimizes cement abrasion.

Without a collar, however, the surgeon is intra-operatively challenged to position these stems both axially and rotationally. A less than ideal position of the stem within the bone, also known as malposition, has been shown to limit the patients range of motion by inducing improper leg length, inadequate lateral stem offset or non-anatomical version of the stem.

Inadequate pressurization of the cement within the femoral canal has also been documented as a potential cause of improper cement technique. Centralization of the stem within the cement mantle is also critical for successful results. Non-uniform or excessively thin cement/stem/bone interfaces may lead to high internal stresses and subsequent cracks. Cement debris generation due to abrasion has also been shown to produce excessive third-body wear of the polyethylene acetabular components as well as potentially induce osteolytic reactions and bone resorptions that may lead to stem loosening. One single femoral stem that can singly address these critical issues is the intended solution.

The proper distribution of stresses within the prosthesis and throughout the surrounding bone is a problem in the use of known hip joint systems. If too little stress is applied to the bone, resorption can occur leading to atrophy of the affected area. Too much stress may result in an undesirable hypertrophy of the affected area. In some prior art, femoral stem designs' excess forces are transmitted through the relatively rigid stem to the distal portion, resulting in hypertrophy of the bone surrounding the distal portion, and atrophy of the bone surrounding the proximal portion of the stem.

Attempts have been made to provide for a proper amount of stress on the cement mantle of prosthesis. For example, in U.S. Pat. Nos. 5,171,275 and 5,290,318 both to Ling, et al, incorporated herein by reference, disclose a tapered, collarless femoral hip joint prosthesis formed of cobalt chromium-molybdenum alloy with a highly polished surface. The stem is tapered in the anterior/posterior and medial/lateral directions and has rounded corners.

The tapered collarless design permits the polished stem to subside within the cement mantle. The taper of the stem permits it to self-tighten upon the slight movement which occurs during the subsidence and engage in the hollow centralizer and yet to do so without pulling the cement mantle and avoiding the disruption of the micro interlocking at the cement bone interface.

This design causes the stem to impart primary compressive forces against the cement mantle thus transmitting the load to the femur. Transmitting the load in this manner forces the cement mantle continuously, snuggly, and firmly against the interior of the femur to assist in maintaining the integrity of microlocking at the cement bone interface.

Utilizing devices such as those shown in Ling without a collar, however, the surgeon is intra-operatively challenged to position the stems both axially and rotationally. The inability to properly position the prosthesis may limit the patient's range of motion by inducing, for example, improper leg length, inadequate lateral stem offset or none anatomical version of the stem. Conversely the inclusion of a collar on the femoral hip joint prosthesis may lessen or eliminate the ability of the femoral stem prosthesis to subside and impart the primary compressive forces against the cement mantle necessary to assure that the cement mantle continuously is snugly and firmly against the interior of the femur to maintain the integrity of the microlocking at the cement bone interface.

The devices as disclosed in the above mentioned Ling patents have been commercialized in the Zimmer CPT™ tapered highly polished stems. Other such stems include the Stryker Howmedica Exeter™ and the C-Stem™ (a DePuy product). These tapered highly polished stems have displayed clinical success, but have done so without the benefits of a collar. Because these designs lack consistent methods of proximal pressurization and centralization, cement mantle variability has been demonstrated. Meanwhile, collared stems such as the Charnley hip and its derivatives have also demonstrated excellent results, but do not have the additional advantage of controlled long-term subsidence.

Tapered highly polished stems have historically been designed without a proximal collar to prevent cement creep and long term, controlled subsidence within the cement mantle while simultaneously minimizing cement abrasion. Without the collar, however, the surgeon is intra-operatively challenged to position the stems both axially and rotationally. This malposition has been shown to limit the patient's range of motion by inducing improper leg length, inadequate lateral stem offset or non-anatomical version of the stem.

Inadequate pressurization of the cement within the femoral canal has also been documented as a potential cause of improper cement technique.

Centralization of the stem within the stem mantle is also critical for success. Non-uniform or excessively thin cement mantles can induce high cement stresses and subsequent cracks that cause failure at the cement-stem-bone interfaces. Cement debris due to abrasions has also been shown to produce excessive third-body of polyethylene acetabular components as well as potentially induce osteolytic reactions and bone resorption that may lead to stem loosening. One single femoral stem that can singularly address these clinical issues is the intended solution.

SUMMARY OF THE INVENTION

Accordingly, a need has arisen for a prosthesis, which optimizes cement pressurization while providing for initial and final stem position.

The present invention is a prosthesis with a resorbable collar. The prosthesis may be a tapered, highly polished femoral prosthesis. The resorbable collar provides initial rotational and axial positioning. The resorbable collar also may provide stem centralization and pressurization. The prosthesis, after the collar has been resorbed, will allow for cement creep and controlled, long term subsidence with minimal cement abrasion.

The present invention provides for a prosthesis that includes a collar which may be assembled with, for example, a femoral hip stem. The collar is preferably made of resorbable material. The collar provides for a mechanical reference for axial and rotational position as well as for pressurization of the cement during insertion. The collar may also include additional geometry for a proximal centralization of the stem within the cement mantle.

A primary purpose of stem collars is proper stem placement with respect to the long bone longitudinal axis. Collars are positioned on the resected end of the long bone and can potentially bear a considerable portion of the patient's weight. Such load carrying of the collar can lead to stress shielding particularly at the proximal medial calcar portion of the resected long bone. The stress shielding leads to bone resorption and bone loss. A resorbable collar may then be used on both cement and uncemented long bone stems to properly position the stem. After the collar is resorbed, the stress shielding and resultant bone loss otherwise caused by a collar may be reduced.

According to one embodiment of the present invention, there is provided an articulating hemiarthroplasty prosthesis. The prosthesis includes a stem for implantation at least partially within the medullary canal of a long bone and a collar. The collar is used for positioning during surgery the prosthesis within the long bone. The collar is operably associated with the stem and extends outwardly therefrom. At least a portion of the collar includes a resorbable material.

According to another embodiment of the present invention there is provided an articulating hemiarthroplasty prosthesis for use with bone cement. The bone cement forms a bone cement mantle over a portion of the prosthesis. The prosthesis includes a stem for implantation at least partially within the medullary canal of a long bone and a collar.

The collar is operably associated with said stem and extends outwardly from the stem. At least a portion of the collar includes a resorbable material. The prosthesis also includes a head and a cup. The cup is used for engagement with the ball. Prior to the resorbing of the resorbable material, the collar is adapted for positioning and supporting the prosthesis within the long bone. Subsequent to the resorbing of the resorbable material, the prosthesis is adapted to provide controlled subsidence of the stem into the cement mantle of the prosthesis.

According to yet another embodiment of the present invention, there is provided a hip stem for use in arthroplasty. The hip system includes a stem for implantation at least partially within the medullary canal of a long bone and a collar. The collar is operably associated with the stem and extends outwardly from the stem. At least a portion of the collar includes a resorbable material.

According to another embodiment of the present invention, there is provided a collar for use with a stem for use in arthroplasty. The collar is extendable outwardly from the stem. At least a portion of the collar includes a resorbable material.

According to a further embodiment of the present invention, there is provided a method for providing total hip arthroplasty. The method includes the steps of resecting a long bone, opening a medullary canal of the long bone, inserting cement into the canal, providing a stem, placing a collar in cooperation with the stem, implanting the prosthesis at least partially within the medullary canal, positioning the collar in proximity with the resected portion of the long bone, permitting the collar to be resorbed, and permitting controlled subsidence of the stem into the cement mantle.

The technical advantages of the present invention include improved cement pressurization by the utilization of the collar. The presence of the collar provides for a sealing interface between the resected bone and the collar. Inadequate pressurization of the cement within the femoral canal has been documented as a potential cause of improper cement technique.

Further, the presence of the collar provides for improved cement stress distribution. The presence of the collar improves the ability of the stem to be centralized within the cement mantle. The centralization of the stem within the cement mantle improves the uniformity of the cement mantle and reduces the likelihood of thin cement mantles. Thin cement mantles may induce high cement stresses and subsequent cracks that cause failure at the cement-bone-stem interfaces.

Further, the improved pressurization and centralization provided by the resorbable collar serves to reduce cement debris due to abrasion. Cement debris due to abrasion has been shown to produce excessive third body wear of polyethylene acetabular components, as well as potentially induce osteolytic reactions and bone resorption that may lead to stem loosening.

Another technical advantage of the present invention is the ability to provide for an accurate initial and final stem position by utilizing the collar to position the stem against the resected portion of the bone. This is applicable to both cemented and uncemented stems, as well as to coated and uncoated stems, including those coated with a porous coating for bone ingrowth.

A further technical advantage of the present invention is the ability of the resorbed collar to alleviate stress shielding and resultant bone loss particularly to the medial calcar otherwise caused by a traditional metal collar.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 19 is a view of the hip stem along the line 19—19 in the direction of the arrows in accordance with the embodiment of the present invention of FIG. 15;

FIG. 20 is a plan view of a resorbable collar of the present invention for use in a hip stem in accordance with the embodiment of the present invention of FIG. 15;

FIG. 20A is a partial auxiliary view of a resorbable collar in accordance with another embodiment of the present invention;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
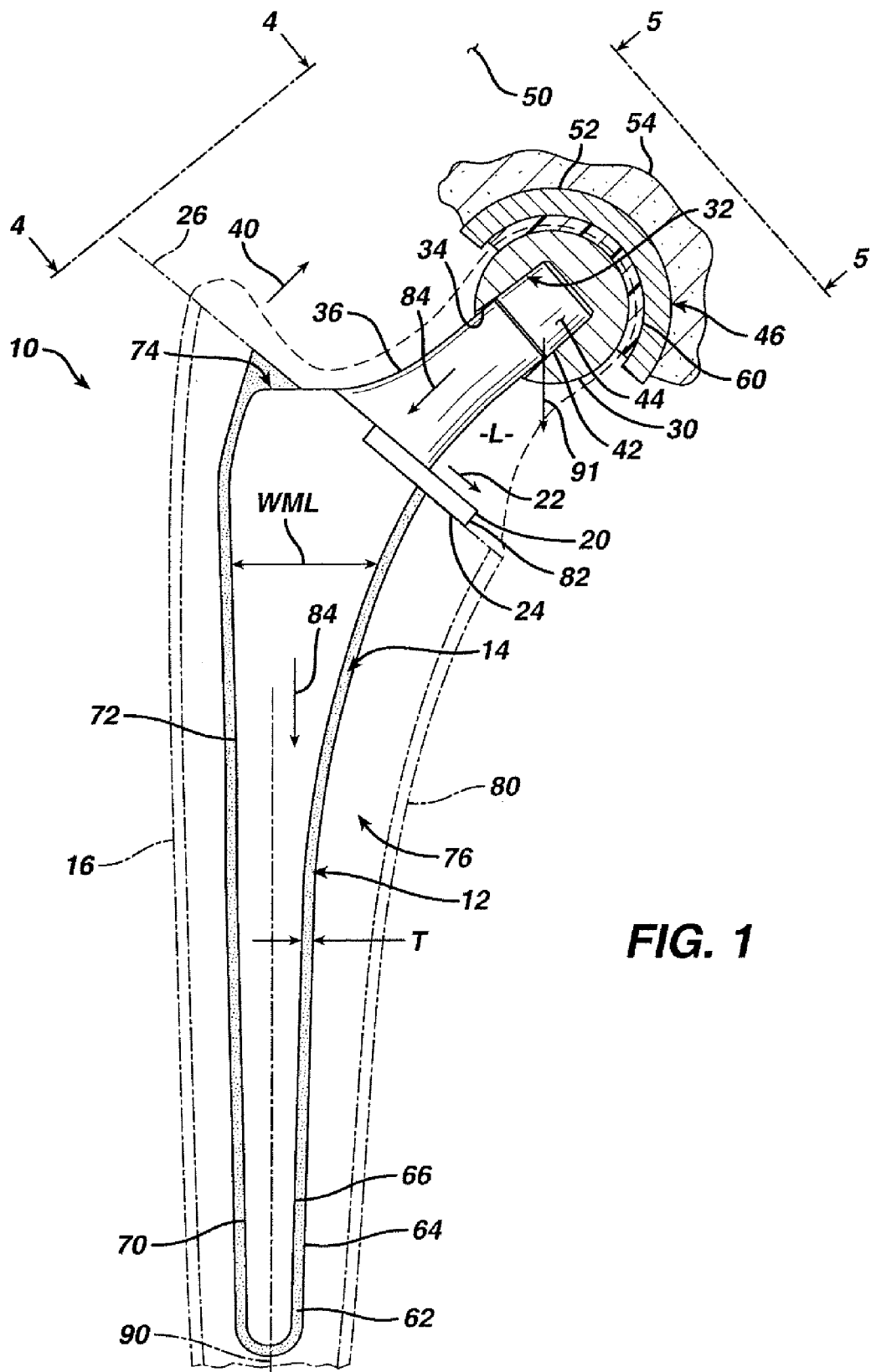
FIG. 1 is a plan view of a hip prosthesis implanted into a femur and an acetabulum in accordance with an embodiment of the present invention.

According to the present invention and referring now to FIG. 1, an embodiment of the present invention is shown as prosthesis 10. The prosthesis 10 includes a stem 12. As shown in FIG. 1, the stem 12 is suitable for implantation at least partially within medullary canal 14 of long bone 16.

The prosthesis 10 further includes a collar 20 for positioning during surgery the prosthesis 10 within the long bone 16. The collar 20 is operably associated with the stem 12 and extends outwardly in the direction of arrow 22 from the stem 12. At least a portion of the collar 20 includes a resorbable material. Preferably and as is shown in FIG. 1, the collar 20 includes a collar face 24 which is positioned against the resected surface 26 of the long bone 16. The collar 20 thus serves to support the prosthesis 10 against the long bone 16 and to provide a reference for proper positioning the prosthesis 10 within the medullary canal 14 over long bone 16.

Preferably and as shown in FIG. 1, the prosthesis 10 preferably further includes a head 30 which is operably associated with the stem 12. The head 30 may be operably associated with the stem in any suitable manner. For example, the head 30 may include a cono-frustical recess 32 forming an internal tapered surface 34. As shown in FIG. 1 the stem 12 may include a neck 36 extending proximally in the direction of arrow 40 from the collar 20. The neck 36 may include an externally tapered portion 42 having an external surface 44. As shown in FIG. 1 the external surface 44 of the portion 42 of the neck 36 is matingly fitted to the internal surface 34 of the head 30.

The prosthesis 10 may further include a cup 46 for pivotal engagement with the head 30. The cup 46 may be secured to hipbone 50 in any suitable fashion. For example, the cup 46 may include a hemispherical outer surface 52 which matingly fits with acetabulum 54 of the hipbone 50. The outer surface 52 of the cup 46 may include openings (not shown) to which fasteners (not shown) are fitted for securement to the acetabulum 54 or may include a threaded periphery (not shown) for engagement with the acetabulum 54.

The cup may be in pivotal engagement with the head in any suitable fashion. For example, the head and the cup may have mating surfaces for metal to metal contact with each other or as shown in FIG. 1, a liner 60 may be pivotably located between the cup 46 and the head 30. The liner 60 may be made of a durable metal or may be made of a non-metal material, for example, a plastic or a ceramic. For example, the liner 60 may be made of a high molecular weight polyethylene. For example, the liner 60 may be made of ultrahigh molecular weight polyethylene. One particular ultrahigh molecular weight polyethylene that is well suited for this application is sold by DePuy as Marathon® and is generally described in U.S. Pat. Nos. 6,017,975 and 6,228,900 which are hereby incorporated by reference in their entireties.

While the present invention may be practiced with a prosthesis having a stem in cementless contact with the long bone 16, preferably, and as shown in FIG. 1, the prosthesis 10 is preferably utilized with bone cement 62 which forms cement mantle 64 over outer periphery 66 of distal portion 70 of body 72 of the stem 12. The cement mantle 64 has a thickness T of for example, 0.5 to 4.5 mm.

Preferably, and as shown in FIG. 1, a cavity 74 is formed in the medullary canal 14 of the long bone 16 to permit the prosthesis 10 to be inserted therein. The cavity 74 may be formed by any of various commonly available methods for preparing the long bone 16 for the prosthesis 10 for example, the cavity 74 may be formed by reaming or by broaching. The cavity 74 is formed to sufficient size to provide for the positioning of the stem 12 and for the presence of the cement mantle 64 between the stem 12 and cancellous bone 76. The outer hard portion of the long bone 16 commonly known as cortical bone 80 is preferably not or minimally reamed or broached to form the cavity 74.

Preferably and as shown in FIG. 1, portion 82 of the collar 20 extending outwardly from the stem 12 in the direction of arrow 22 is preferably adapted to be resorbed by the body to provide control subsidence of the stem 12 into the cement mantle 64 of the prosthesis 10 after the resorption of the collar. As shown in FIG. 1, resorption of the collar 20 will permit the movement of the stem 12 of the prosthesis in the direction of arrow 84.

It should be appreciated that the invention may be practical without the cement mantle 64. In an application without the use of cement, the cavity 74 is sized to fit the prosthesis 10. An uncemented stem may or may not include surface coating or treatments including possibly a bone ingrowth coating such as Porocoat®, a product manufactured by the assignee of the present invention.

Preferably and as shown in FIG. 1, the body 72 of the stem 12 preferably has a shape adapted to provide control subsidence of the stem 12 into the cement mantle 64 of the prosthesis 10. While a variety of shapes of the body 72 of the stem 12 may provide for control subsidence of the stem 12 preferably and as shown in FIGS. 1 and 2 the width of the body 72 steadily decreases in the direction arrow 84 along axis 90 of the body 72.

Figure 2:
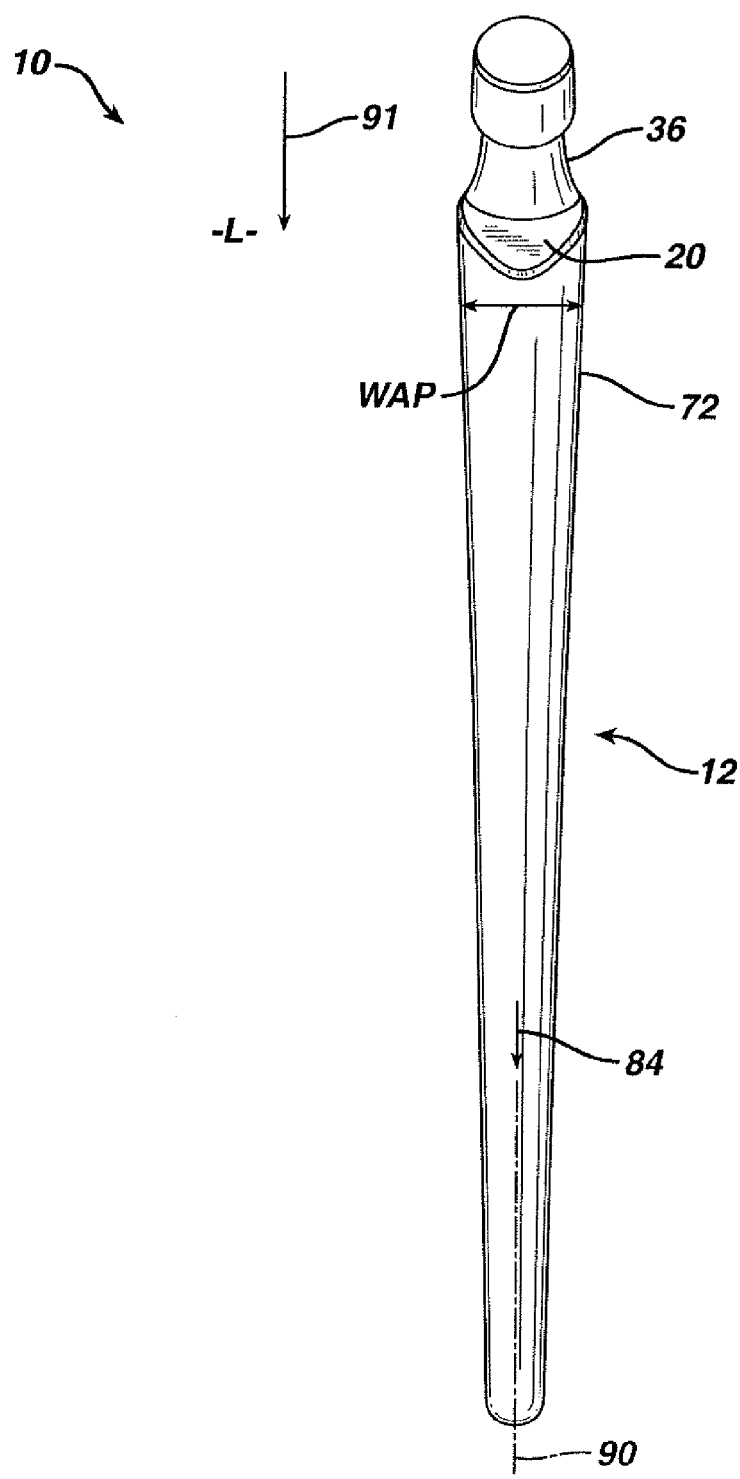
FIG. 2 is a medial end view of a hip stem in accordance with the embodiment of the present invention of FIG. 1.

Referring to FIGS. 1 and 2, not only does the medial lateral width (WML) of the body 72 preferably decrease in the direction of arrow 84, the anterior posterior width (WAP) preferably also decreases in the direction of arrow 84 along axis 90. The tapering in of the stem 12 in the direction distally of arrow 84 in combination with the force of load L in the direction of arrow 91 downwardly, the body 72 of the prosthesis upon resorption of the collar 20 moves or subsides in the direction of arrow 84 maintaining the pressure on the cement mantle 64. Such continual pressure on the cement mantle serves to promote bone growth and reduce osteolysis.

The stem 12 may be made of any suitable or durable material which is biocompatible and clinically proven. For example, the stem may be made of a durable metal for example, a cobalt-chromium-molybdenum alloy, a stainless steel alloy or a titanium alloy. Preferably, the outer periphery 66 preferably has a surface finish which is conducive to permitting cement creep and controlled long-term subsidence. Preferably thus, the outer periphery 66 of the stem 12 should be polished. For example, the outer periphery 66 of the stem may have optimally a surface finish RA of less than or equal to 15 micro-inches.

The collar 20 may have any suitable shape of its outer periphery provided that the collar 20 serves to support the prosthesis 10 along at least a portion of the resected surface 26 of the long bone 16. For example, the collar geometry may take the form of those commonly seen on currently marketed prosthesis.

The collar material is preferably made of a resorbable and biocompatible material. Many materials fall into this category and include such materials as PLA (polylactic), PGA (polyglyolide) or vitamin E derivatives. Vitamin E derivatives are available and are similar to those materials such as in the DePuy Biostop G product line. The Biostop G material is a mixture of neutral components. These neutral components include glycerol, gelatin and water. This combination of glycerol, gelatin and water may be totally reabsorbed within 15 days of surgery.

Other materials which may be suitable for the bioresorbable collar include monomers and biodegradable polymers.

Monomers include L-lactide, D-lactide, DL-lactide and glycolide. L-lactide is produced by the depolymerization of low molecular weight poly, made by condensation polymerization of the corresponding L (+) lactic acid.

DL-lactide is produced by the depolymerization of low molecular weight poly, made by condensation polymerization of the corresponding DL-lactic acid.

D(+) lactide is produced by the depolymerization of low molecular weight poly (D-lactic acid), made by condensation polymerization of the corresponding D-lactic acid.

Glycolide is produced by the depolymerization of low molecular weight poly (glycollic acid), made by condensation polymerization of the corresponding glycollic acid (hydroxyacetic acid).

Polymers include two basic categories known as PLA or polylactide. PLA or polylactide include poly(1)-lactide (poly (d)-lactide, and poly(dl)-lactide).

Copolymers include poly(1)-lactide-co-d-lactide, poly (1)-lactide-co-dl-lactide and poly(lactide)-co-glycolide.

Bioresorbable materials, when in the form of polymers, resorb through the use of two types of biodegradation. The first of this type includes the rapid loss of polymer mass. This type of degradation, when the rate at which the water penetrates the device exceeds that at which the polymer is converted into water-soluble materials, (resulting in erosion throughout the device) is called bulk erosion. All of the commercially available synthetic devices degrade by bulk erosion.

A second type of biodegradation known as surface erosion, occurs when the rate at which the polymer penetrates the device is lower than that of the rate of conversation of the polymer and to water-soluble materials. Surface erosion results in the device thinning over time while maintaining its bulk integrity. Polyanhydrides and polyorthoesters are examples of materials that undergo this type of erosion, when the polymer is hydrophobic, but the chemical bonds are highly susceptible to hydrolysis. In general, this process is referred to as bioerosion rather than biodegradation.

The degradation-absorption mechanism is the result of many inter-related factors, including the stability of the polymer backbone, the presence of catalyst additives and impurities or plasticizers and the geometry of the collar. Preferably, the collar is designed by utilizing materials and geometry to balance these factors by tailoring a collar to slowly degrade and transfer stress at the appropriate weight to surrounding tissues as they heal.

Applicants believe that a bioresorbable collar may be designed having a resorption rate varying from as little as a few weeks to as long as one year or more. For example, when utilizing vitamin E derivatives such as that of the Biostop G product, resorption rates of a few weeks would occur. Conversely, when using materials such as PLA and PGA the resorption rates may be respectively as great as 24 months or 6 months.

The physical properties of PLA and PGA may be particularly well suited for this application in that PLA has sufficient physical properties to maintain the loads required in such prosthesis. For example, PLA has a tensile strength from 4 to 12,000 psi and PGA has a tensile strength of 10,000 psi or greater.

Preferably, the bioresorbable polymers for use as materials for the collar of the present invention are thermoplastic. These thermoplastic materials can be processed into different product shapes using conventional plastic processing techniques for example, extrusion and injection molding. The process and conditions depend on the particular polymer and inherent viscosity. It is recommended that the polymers be thoroughly dried before malprocessing using suitable drying conditions.

The bioresorbable materials for use in the collar are preferably sterilized. The most commonly used sterilizing methods for such polymers, for example, lactide/glycolide type polymers are gas sterilization (ethylene oxide, ETO) and gamma sterilization. ETO sterilization does not substantially effect the molecular properties of these polymers. Care must be taken that gas residues are sufficiently removed from the material. Gamma radiation is known to result in a significant decrease in the molecular weight of these polymers. This effect should be taken in account during the development phase of the collar.

Due to the biodegradable nature of the polymers for use as materials for the bioresorbable collar (storage conditions below 0° centigrade/32° Fahrenheit should be maintained, preferably at −15° centigrade or 5° Fahrenheit or at a lower temperature. The cold storage serves as an additional precaution against hydrolysis loss. Before use, the package should be allowed to reach room temperature to avoid condensation of atmospheric moisture. When opened, the material should be used as quickly as possible and be sealed, after purging with high purity dry nitrogen, in order to keep out atmospheric moisture.

Preferably, since the resorbable material in the collar is biodegradable and thus affected by the atmospheric conditions, the length of storage of the bioresorbable collar and the conditions, including temperature and atmosphere in which the bioresorbable collar is stored, should be carefully controlled. The metal stem and other components of the prosthesis of the present invention do not require the same precautions for degradation of the material as the bioresorbable collar. Thus, and as shown in the drawings, the bioresorbable collar is designed to be installed into the prosthesis near the location in which the orthopaedic surgery is to be performed, for example, in or near the operating room.

For example, the collar may be inserted onto the stem or assembled thereto by either advancing the collar radially inward toward the stem or advancing the collar axially in a distal direction toward the indentation of the stem.

Figure 3:
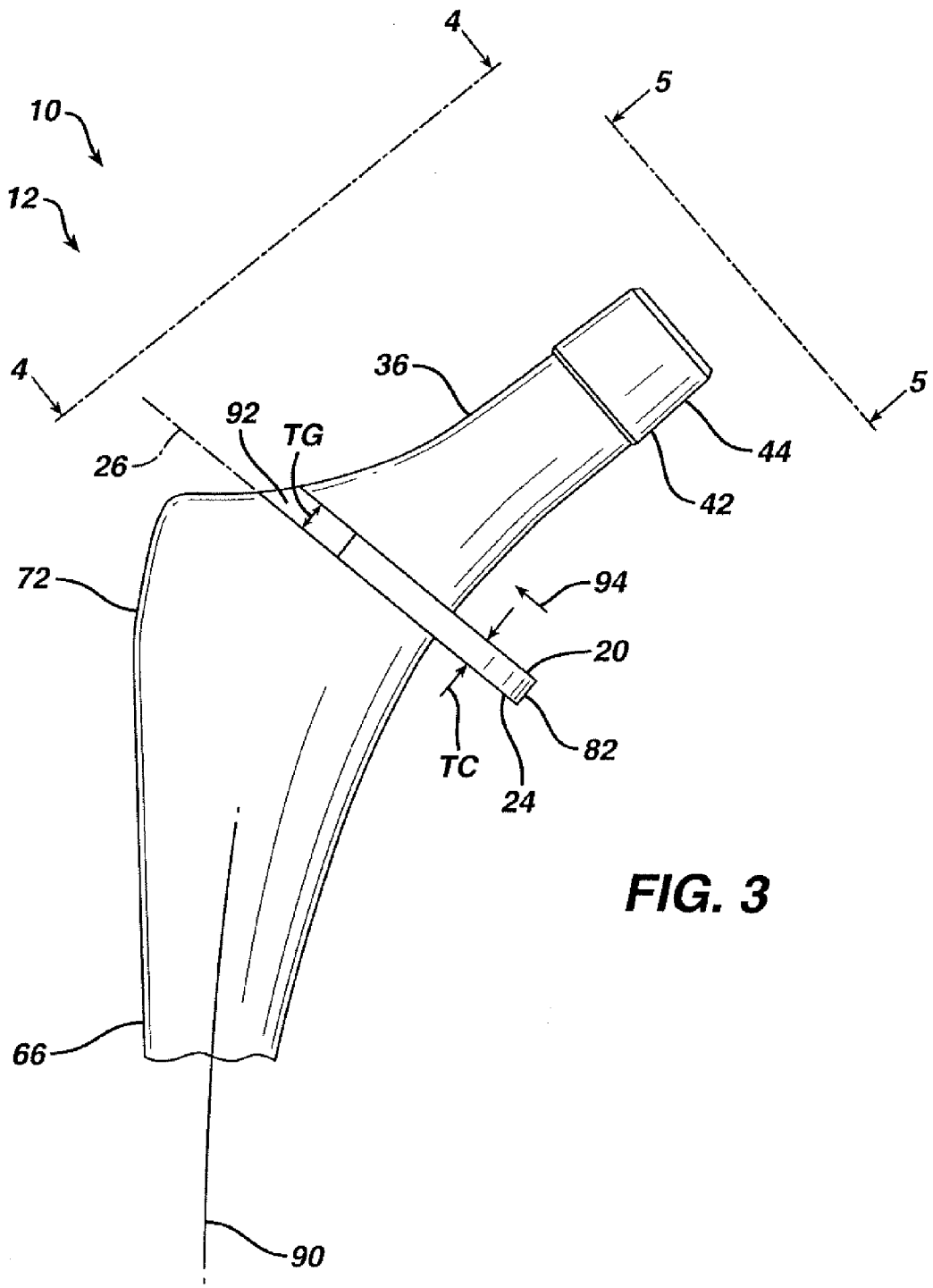
FIG. 3 is a partial plan view of the hip stem in accordance with the embodiment of the present invention of FIG. 1.

An example of the prosthesis according to the present invention where the collar is inserted onto the stem by advancing the collar radially inward toward the stem is shown in FIGS. 1–10. Referring now to FIGS. 2 and 3, the stem 12 may include an indentation or groove 92 positioned between the body 72 of the stem 12 and the neck 36. The indentation or groove 92 is preferably positioned such that face 24 of the collar 20 when inserted into the groove 92 is positioned along the resection line 26.

While the indentation 92 may have any suitable form, preferably the indentation 92 is in the form of a groove. The groove 92 preferably has a width TG which corresponds with the thickness TC of the collar 20. The collar 20 is insertable onto the stem 12 by advancing the collar 20 in the direction of arrow 94. The respective width TC and TG of the collar and groove respectively are sized for proper securing of the collar 20 and may, for example, provide for a sliding fit of the collar 20 or for a slight interference fit therewith.

It should be appreciated that by providing the insertable collar 20, the stem 12 and the collar 20 may be separately packaged such that the storage requirements of the stem 12 and the storage shelf life requirements of the collar may be optimized.

Figure 4:
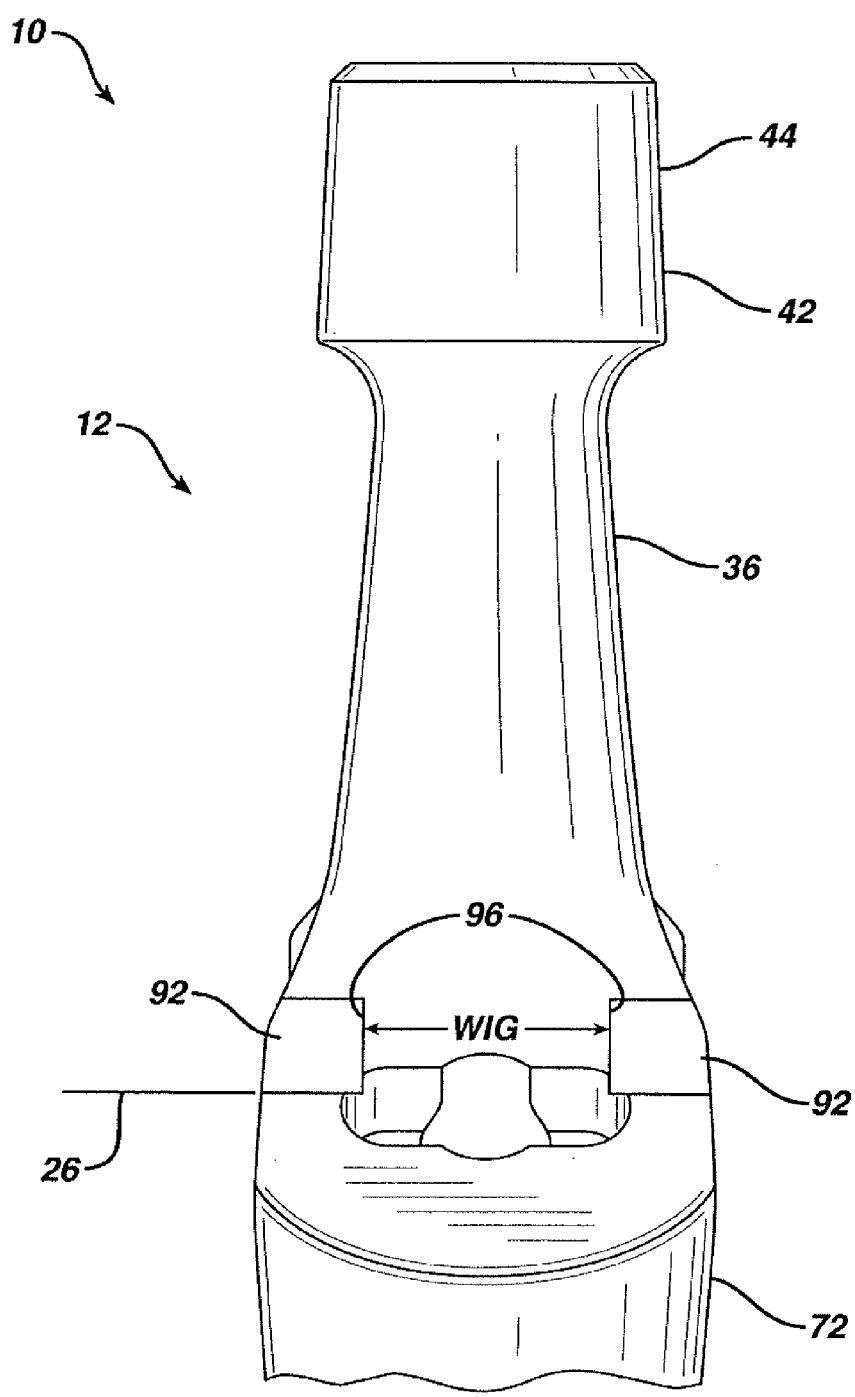
FIG. 4 is view of the hip stem along the line 4—4 in the direction of the arrows in accordance with the embodiment of the present invention of FIG. 1.

Referring now to FIG. 4, the stem 12 is shown in an anterior/posterior view with the groove 92 located on the stem 12. The groove 92 includes inner faces 96 to which the collar 20 may be matingly fitted.

Figure 5:
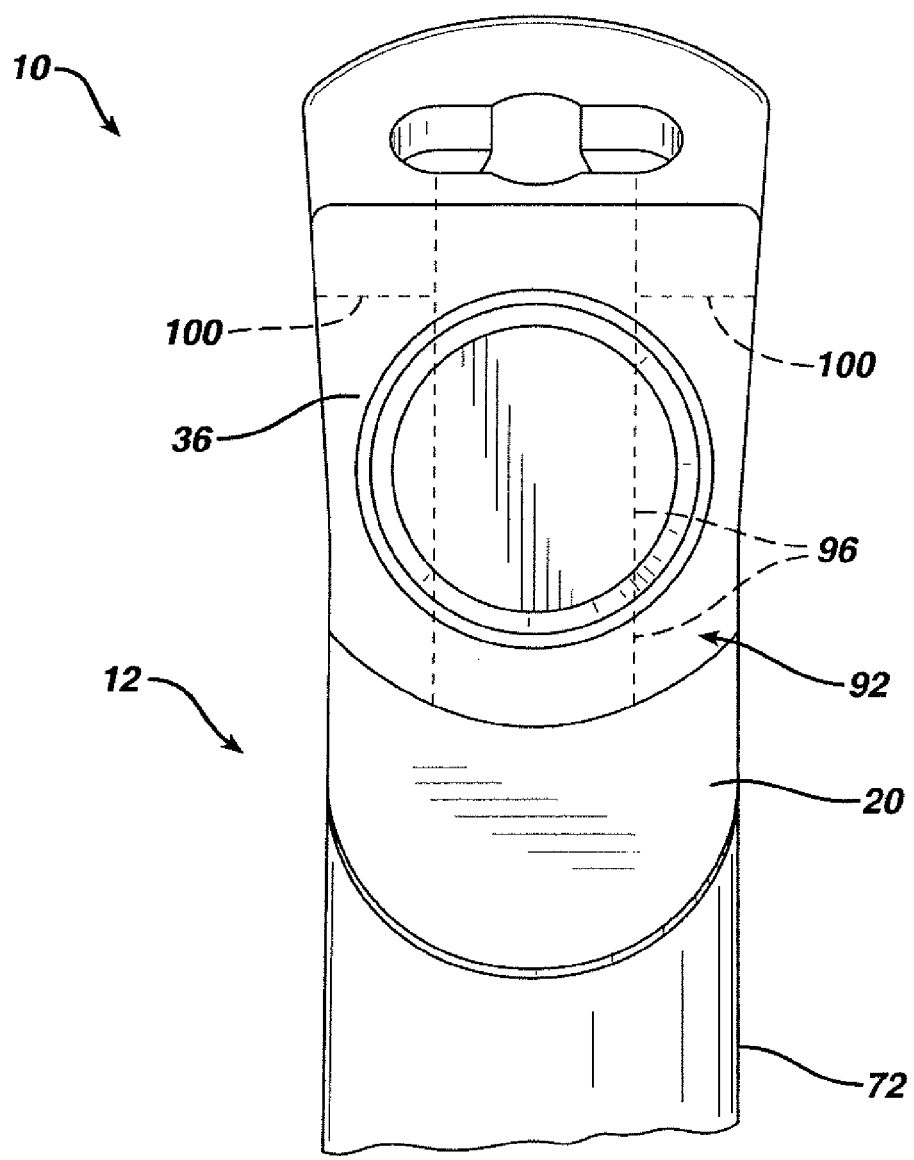
FIG. 5 is view of the hip stem along the line 5—5 in the direction of the arrows in accordance with the embodiment of the present invention of FIG. 1.

Referring now to FIG. 5, a view of the hip stem 12 is shown along the line 5—5 in the direction of arrows in accordance with the embodiment of the present invention of FIG. 1. The anterior/posterior boundaries 96 and medial/lateral boundaries 100 of the groove 92 are shown as hidden lines.

Figure 6:
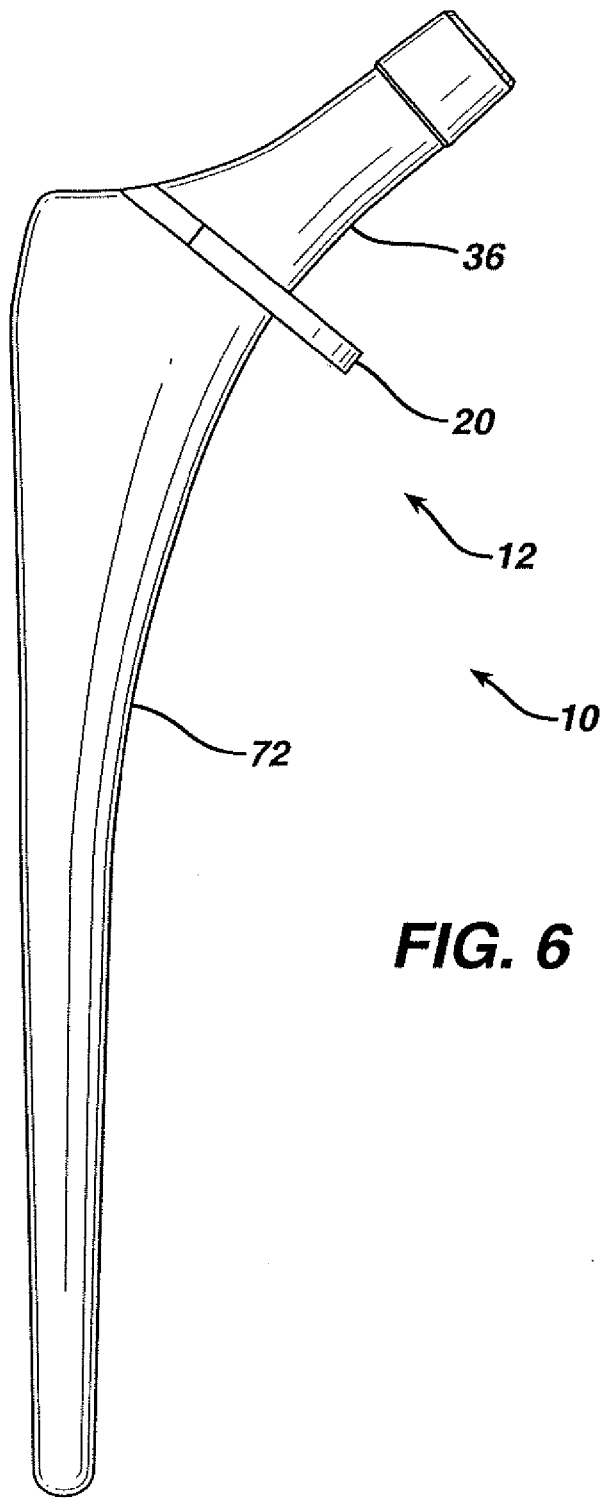
FIG. 6 is a plan view of a hip stem in accordance with the embodiment of the present invention.
Figure 7:
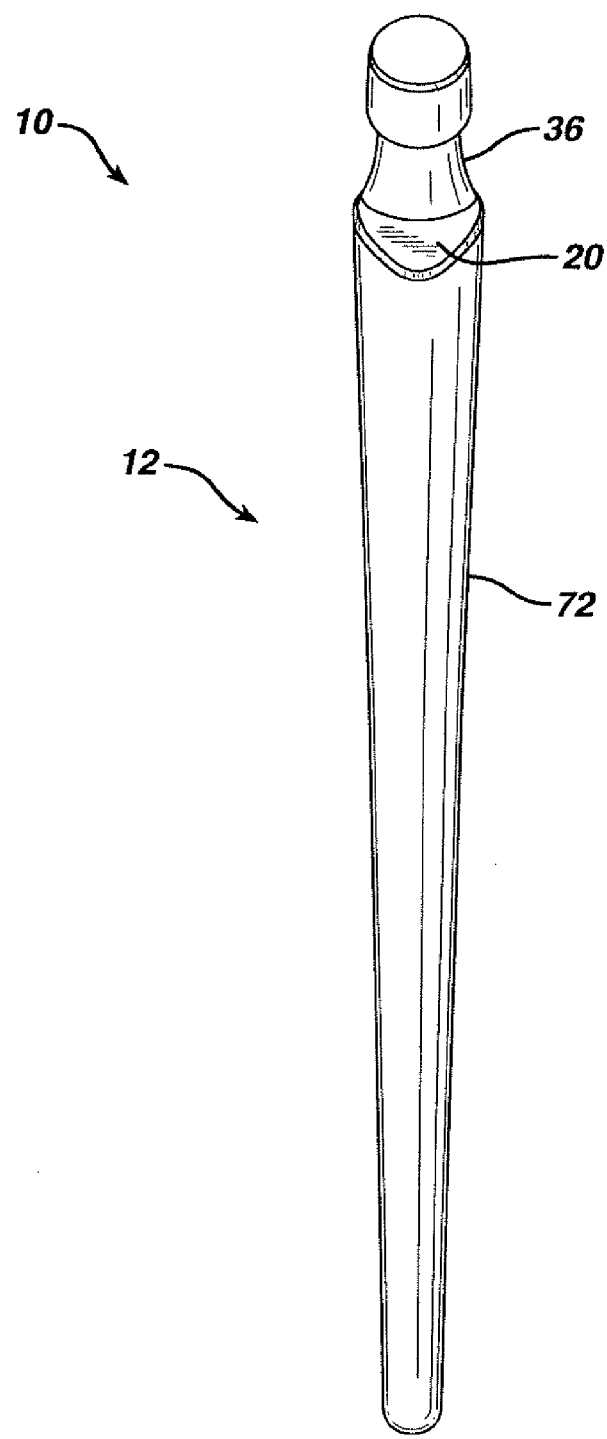
FIG. 7 is a medial end view of the hip stem in accordance with the embodiment of the present invention of FIG. 6.

Referring now to FIGS. 1, 6 and 7, an anterior/posterior view and a medial/lateral view of the prosthesis 10 including the stem 12 and the collar 20 are shown.

Figure 8:
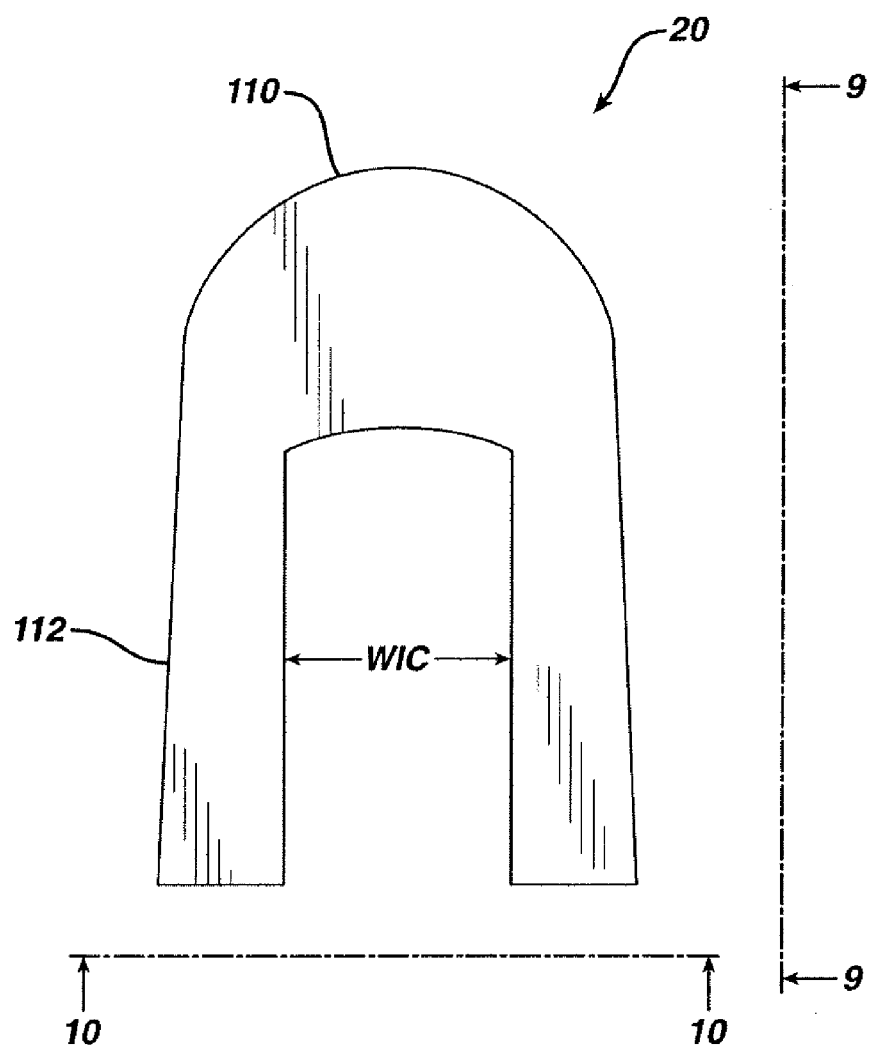
FIG. 8 is a plan view of a resorbable collar of the present invention for use in a hip stem in accordance with the embodiment of the present invention of FIG. 1.

Referring now to FIG. 8, a plan view of the resorbable collar 20 of the present invention for use in the hip stem 12 in accordance with the embodiment of the present invention of FIG. 1 is shown. The collar 12 includes an arcuate medial portion 110 and a pair of arms 112 extending therefrom. The arms 112 are separated by a distance WIC corresponding to the WIG between inner faces 96 of the groove 92 (see FIG. 4).

Figure 9:
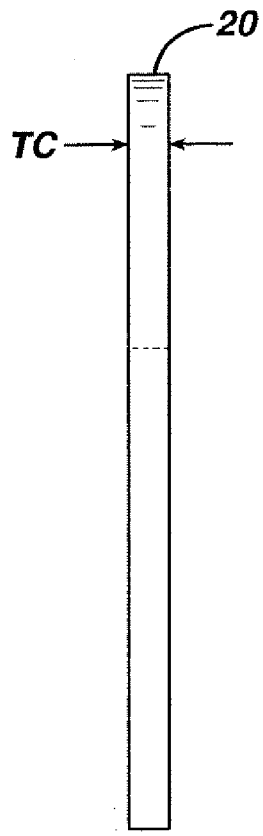
FIG. 9 is view of the resorbable collar of FIG. 8 along the line 9—9 in the direction of the arrows.
Figure 10:
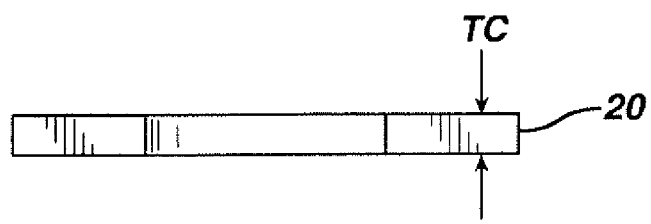
FIG. 10 is view of the resorbable collar of FIG. 8 along the line 10—10 in the direction of the arrows.

Referring now to FIGS. 9 and 10, the collar 20 may, as shown, be planer and having a thickness (TC) corresponding to the thickness (TG) of the groove 92 (see FIG. 3).

Referring now to FIGS. 11 through 22 another embodiment of the present invention is shown as prosthesis 210. With prosthesis 210, the collar is inserted onto the stem by advancing the collar axially in a distal direction toward the indentation of the stem.

Figure 11:
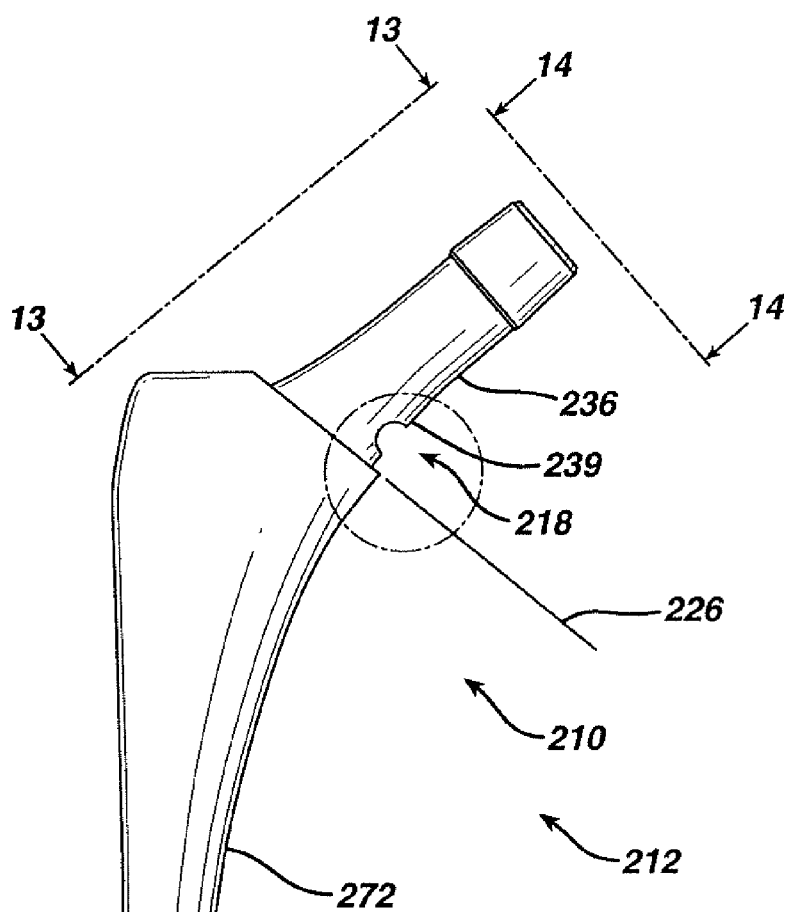
FIG. 11 is a plan view of a hip stem shown without the resorbable collar in accordance with a further embodiment of the present invention having a locking feature to secure the collar to the stem.
Figure 18:
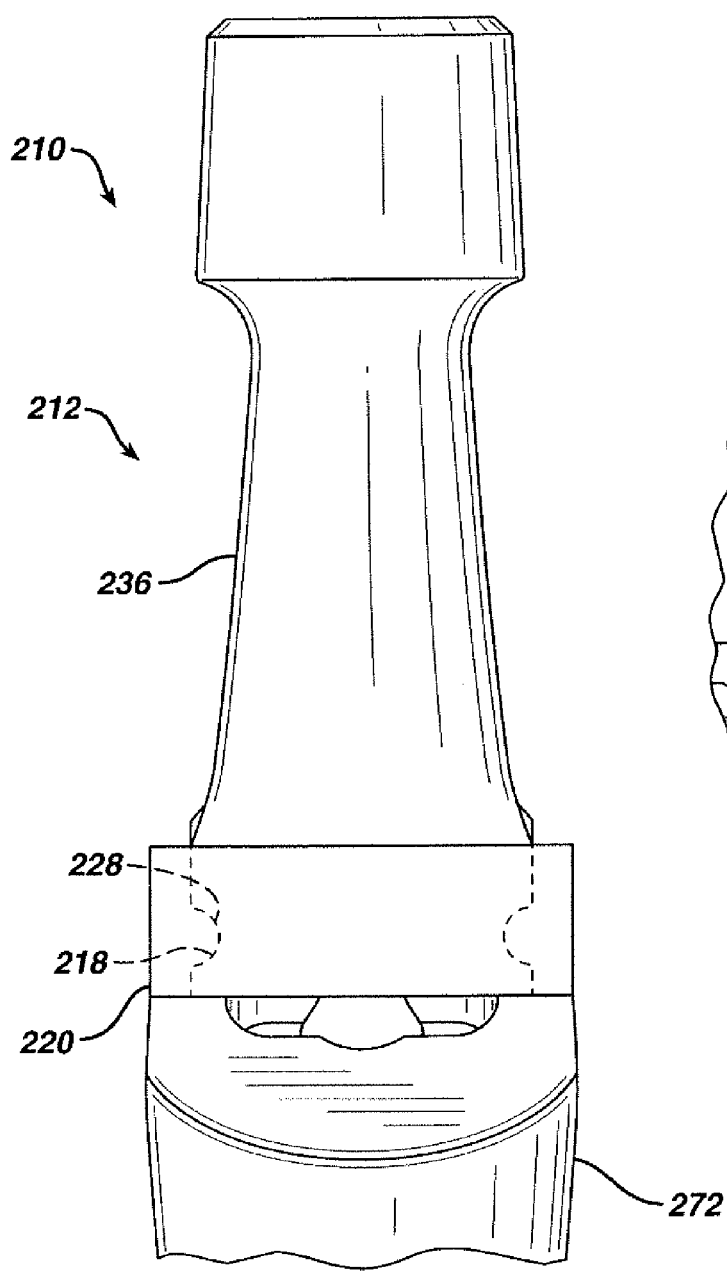
FIG. 18 is a view of the hip stem along the line 18—18 in the direction of the arrows in accordance with the embodiment of the present invention of FIG. 15.

Referring now to FIG. 11, prosthesis 210 is similar to prosthesis 10 of FIG. 1 except that prosthesis 210 includes a locking feature 218 in stem 212 which mates with a locking feature 228 in collar 220 (see FIG. 18). The locking feature as shown in FIG. 11 is preferably on the medial side where loads on the collar will be the greatest. It should be appreciated that the locking feature may be positioned on the lateral side, the anterior side, or the posterior side or any combination thereof.

The stem 212 is similar to stem 12 and is made of a similar suitable durable material. The stem 212 includes a body 272 and a neck 236. The neck 236 extends from the body 272 at resection surface 226.

Preferably and as shown in FIG. 11, the locking feature 218 of the stem 212 of the prosthesis 210 is preferably positioned on outer periphery 239 of the neck 236 near the resection surface 226.

Figure 15:
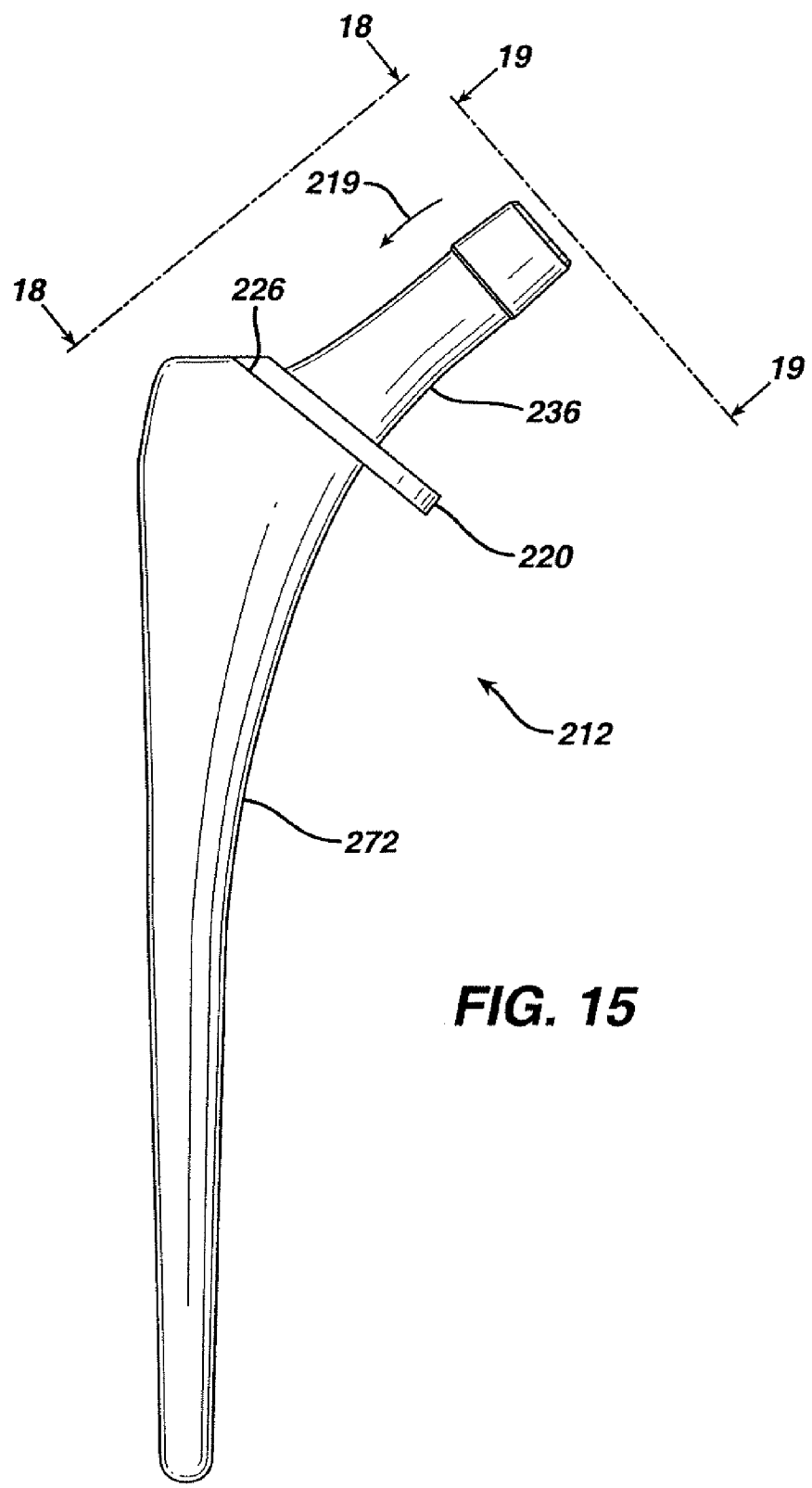
FIG. 15 is a plan view of the hip stem of FIG. 11 with the resorbable collar installed.

The locking feature 218 may be in any suitable form to provide for a locking feature between the stem 212 and the collar 220 (see FIG. 15). For example, and as shown in FIG. 11, the locking feature 218 of the stem 212 may be in the form of a dimple 218. The dimple 218 may be, for example, a generally hemispherical cavity or depression on the periphery 239 of the neck 236 of the stem 212. While in FIG. 11 a solitary dimple 218 is shown, it should be appreciated that a plurality of dimples may be preferred.

Figure 12:
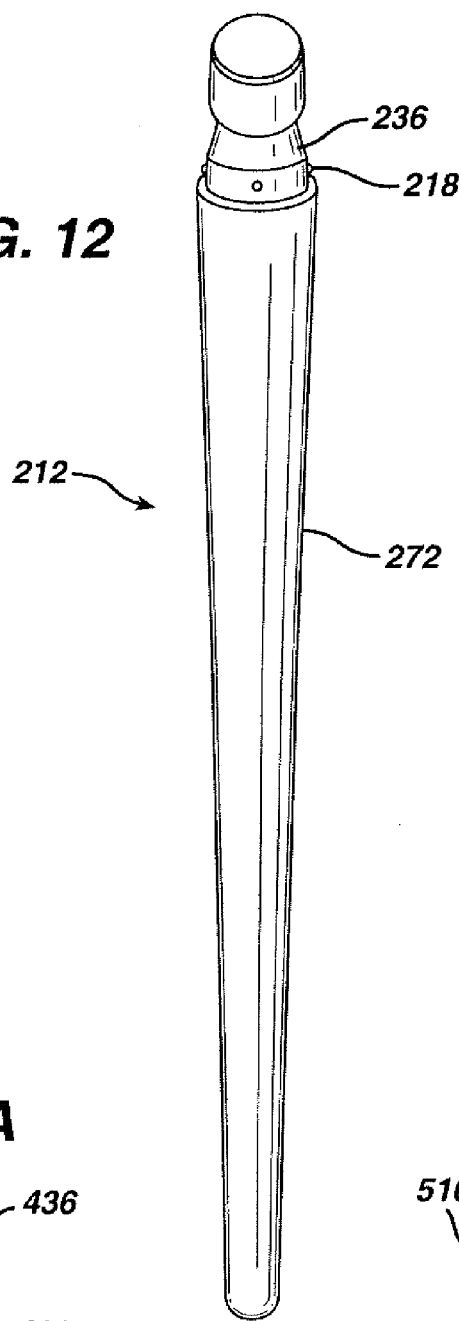
FIG. 12 is a medial, end view of the hip stem in accordance with the embodiment of the present invention of FIG. 11.

Referring now to FIG. 12, the stem 212 of the prosthesis 210 is shown in the posterior/anterior plane. The neck 236 of the body 272 shows a plurality of dimples 218 thereon.

Figure 13:
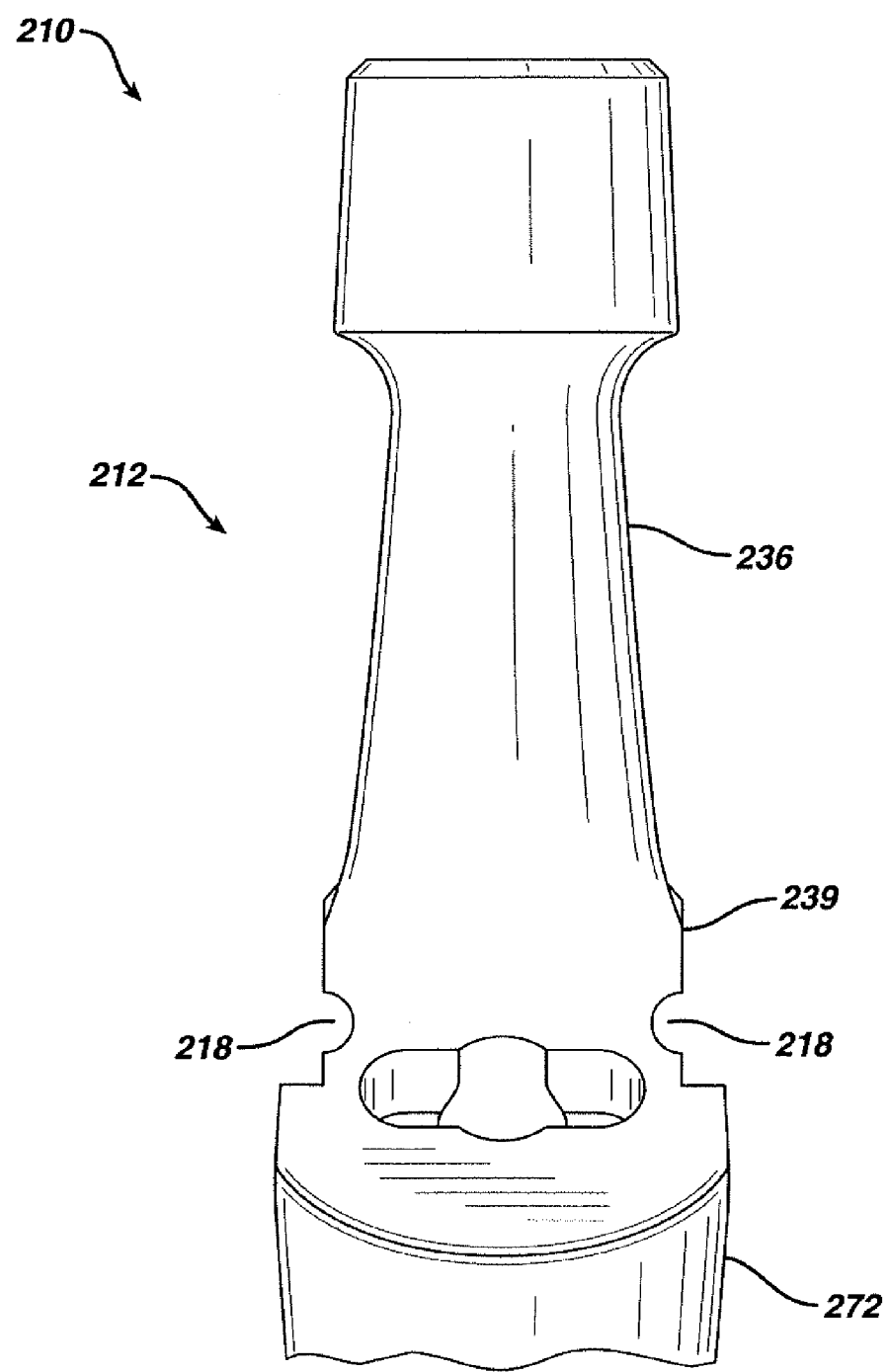
FIG. 13 is a view of the hip stem along the line 13—13 in the direction of the arrows in accordance with the embodiment of the present invention of FIG. 11.

Referring now to FIG. 13, the neck 236 of the stem 212 is shown in greater detail. The neck 236 includes opposed dimples 218 located on outer periphery 239 of the neck 236.

Figure 14:
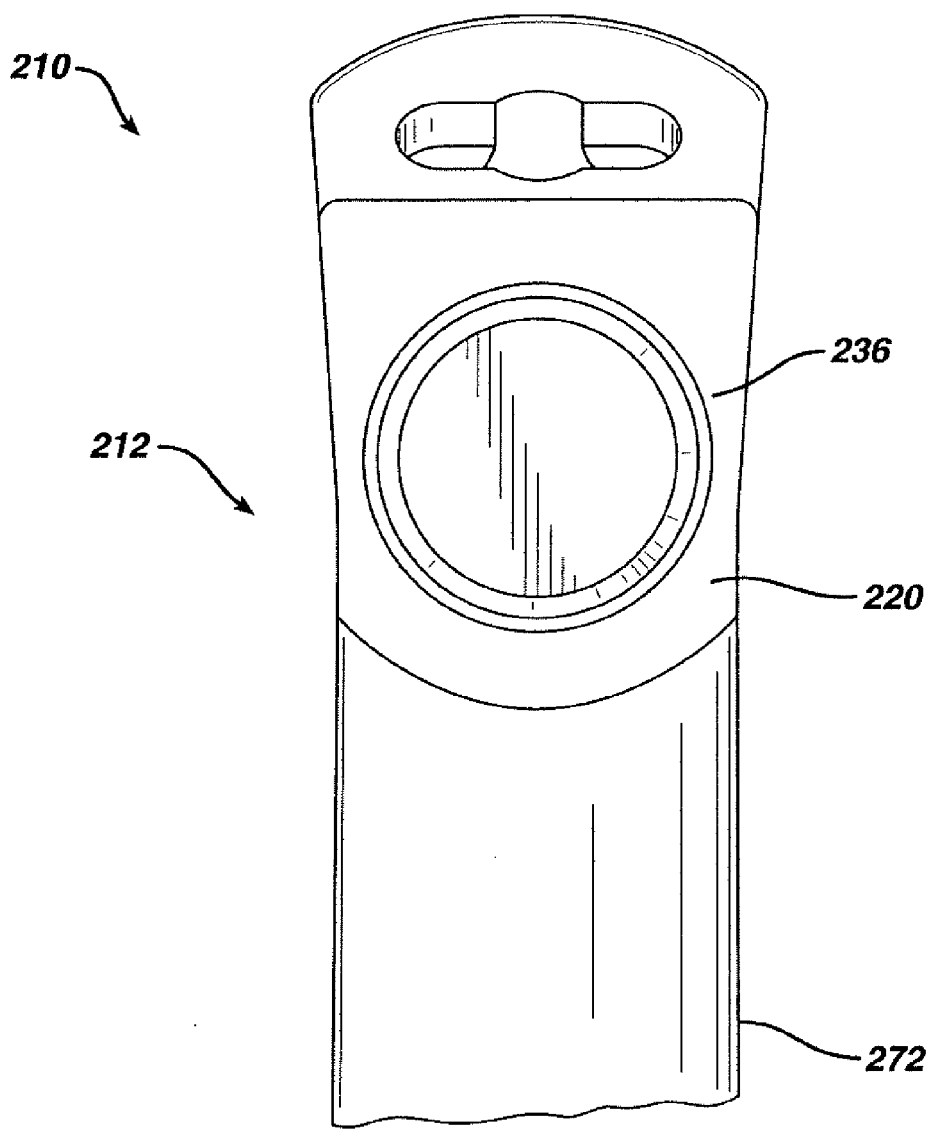
FIG. 14 is a view of the hip stem along the line 14—14 in the direction of the arrows in accordance with the embodiment of the present invention of FIG. 11.

Referring now to FIGS. 14 and 15, a resorbable collar 220 according to the present invention is located positioned on the stem 212. The collar 220 is installed by advancing it distally in the direction of arrow 219 against resection surface 226 of the body 272 of the stem 212.

Figure 16:
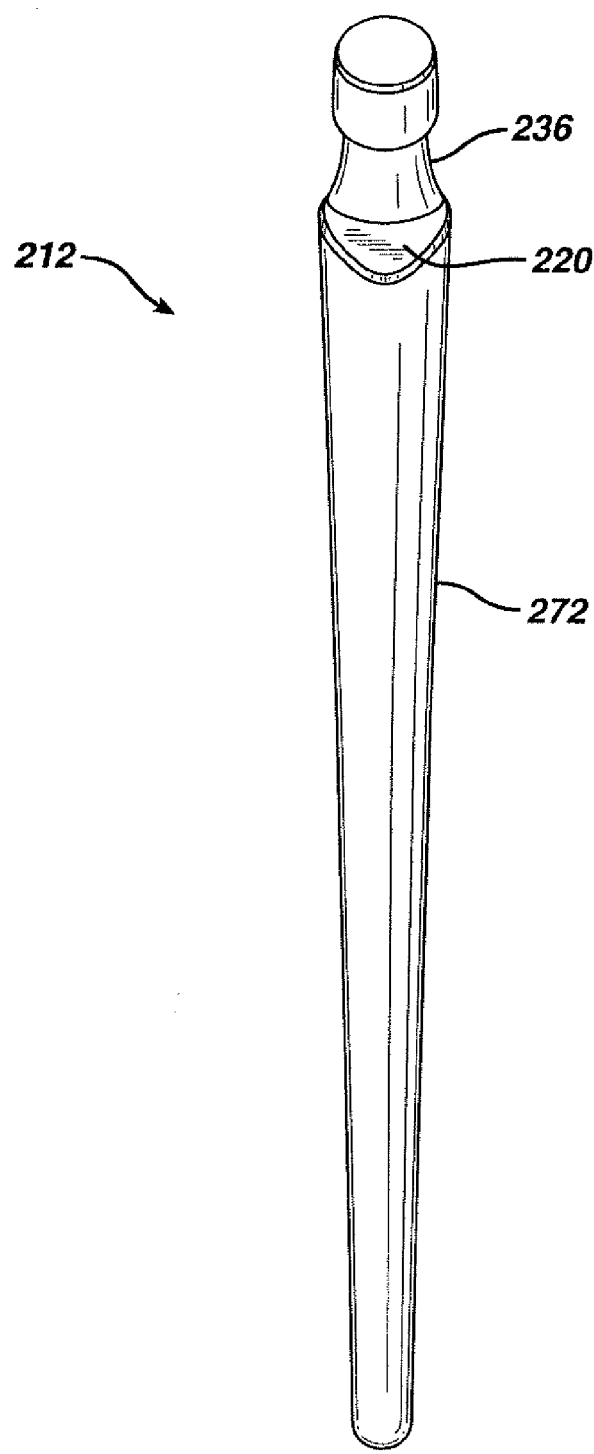
FIG. 16 is a medial end view of the hip stem in accordance with the embodiment of the present invention of FIG. 15.
Figure 17:
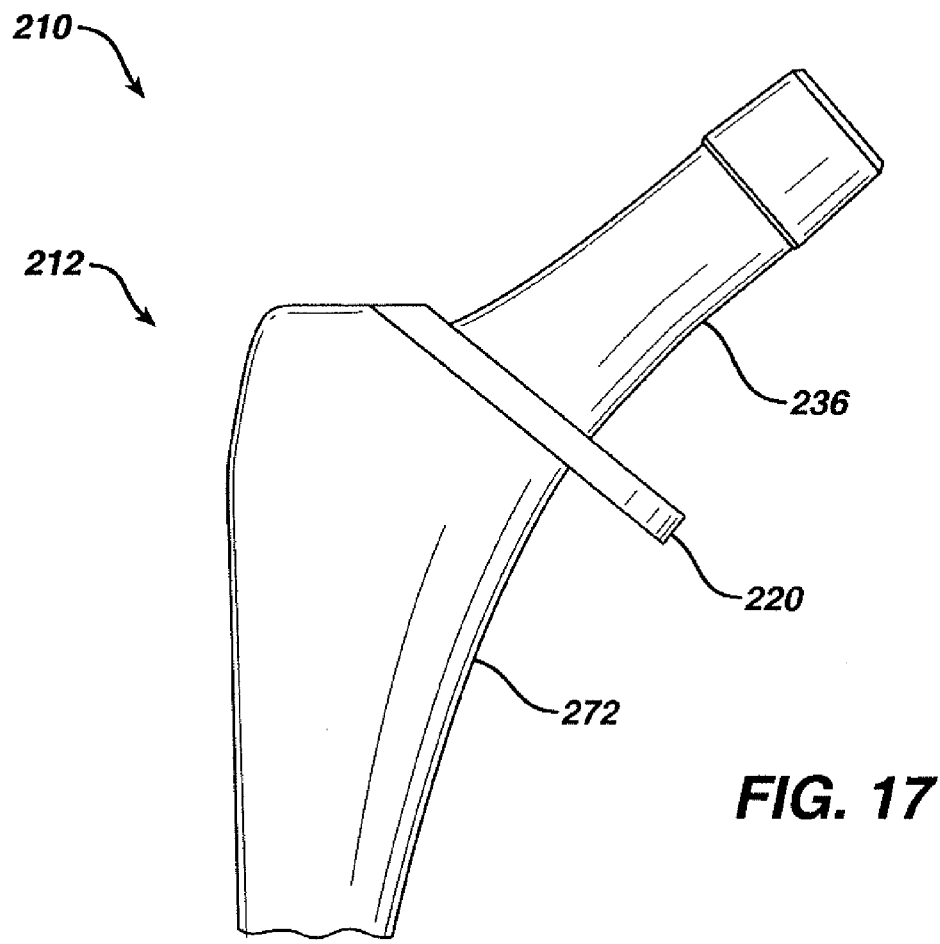
FIG. 17 is a partial plan view of the hip stem in accordance with the embodiment of the present invention of FIG. 15.

Referring now to FIG. 16, the collar 220 as shown installed onto the stem 212. The collar 220 is located between body 272 and the neck 236. At least a portion of the collar 220 extends out beyond the body 272 and provides a support for the stem 212 when installed against a resected long bone (not shown).

Referring now to FIG. 14, the collar is shown enlarged and positioned between the neck 236 and the body 272.

Referring now FIGS. 18 and 19, the locating feature for use with the prosthesis of the present invention including the resorbable collar is shown in prosthesis 210 as dimple 218 on stem 212 which mates with bump 228 on the collar 220. The collar 220 is positioned between the body 272 and the neck 236. As shown in FIG. 18, the prosthesis 210 may include a pair of opposed bumps 228 which mate with a pair of opposed dimples 218 on the stem 212.

Figure 21:
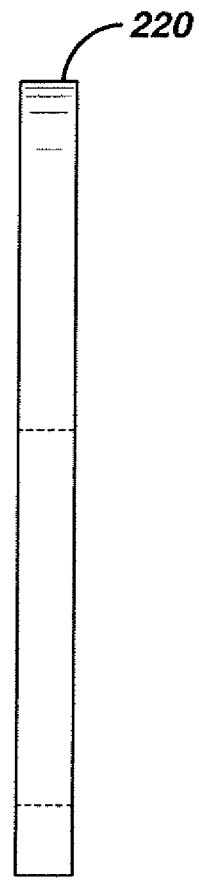
FIG. 21 is a view of the resorbable collar of FIG. 20 along the line 21—21 in the direction of the arrows.
Figure 22:
FIG. 22 is a view of the resorbable collar of FIG. 20 along the line 22—22 in the direction of the arrows.

Referring now to FIGS. 20, 21 and 22, the collar 220 for use with the stem 212 to provide prosthesis 210 of FIG. 18 according to the present invention is shown. The collar 220 includes an internal opening 249 to permit the collar 220 to fit against outer periphery 239 of the neck 236 of the stem 212 (see FIG. 13). The collar 220 includes locking features in the form of bumps extending inwardly from the collar 220 at the periphery of the hole 249. As shown in FIG. 20, four diametrically opposed bumps 228 are located on the collar 220.

Figure 11A:
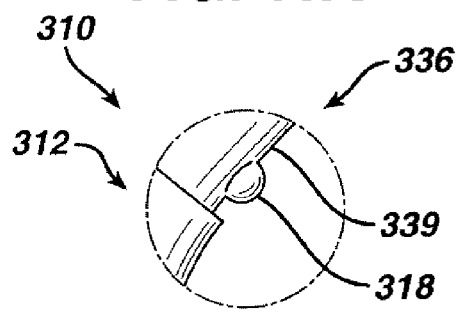
FIG. 11A is a partial plan view of a stem of a further embodiment of the present invention showing a reverse configuration of the locking feature of FIG. 11.
Figure 18A:
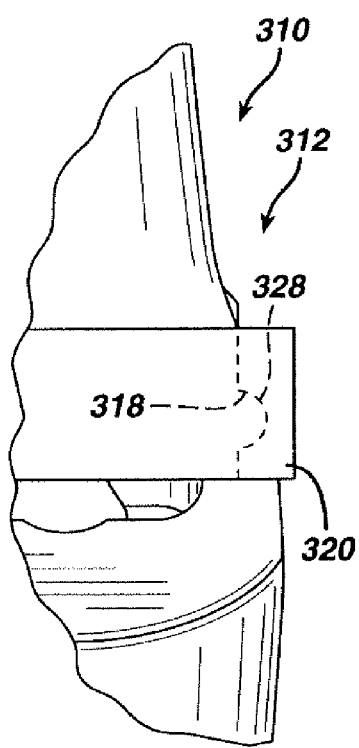
FIG. 18A is a partial auxiliary view of a hip stem in accordance with another embodiment of the present invention.

Referring now to FIGS. 11A, 18A and 20A, an alternate embodiment of the present invention is shown as prosthesis 310 including stem 312. The prosthesis 310 includes an alternate configuration for the locking feature. This alternate configuration is in the form of a bump 328 formed on outer periphery 339 of neck 336 of the prosthesis 310.

Referring now to FIG. 18A the stem 312 of the prosthesis 310 includes the bump 328 which mates with dimple 318 located on collar 320.

Referring now to FIG. 20A the dimple 318 extends outwardly from the hole 349 on the collar 320.

Figure 12A:
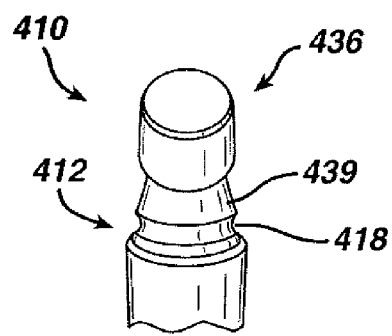
FIG. 12A is a medial, end view of a stem of a further embodiment of the present invention showing a groove configuration of the locking feature of FIG. 12.

Referring now to FIG. 12A, an alternate embodiment of the present invention is shown as prosthesis 410 including stem 412 having a locking feature in another form. For example, as shown in FIG. 12A, the locking feature is in the form of a groove 418 located on the outer periphery 439 of the neck 436 of the stem 412 of the prosthesis 410. It should be appreciated that the groove 418 of the stem 412 of the prosthesis 410 may be utilized in connection with either bumps or an internal rim extending from the hole of the collar (not shown).

Figure 12B:
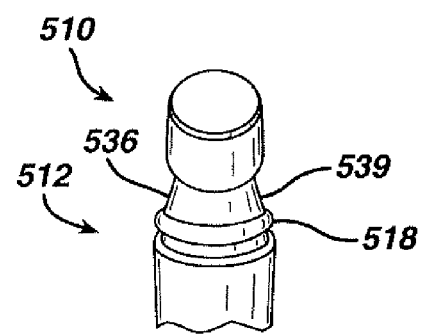
FIG. 12B is a medial, end view of a stem of a further embodiment of the present invention showing a rim configuration of the locking feature of FIG. 12.

Referring now to FIG. 12B, an alternate embodiment of the present invention is shown as prosthesis 510 including stem 512 having a locking feature in another form. The locking feature of FIG. 12B for use with the resorbable collar prosthesis of the present invention is in the form of a rim 518. The rim 518 extends outwardly from external periphery 539 of neck 536 of the stem 512 of the prosthesis 510. The rim 518 may cooperate with an internal groove located on the hole of the collar (not shown) or merely provided interference fit with the hole of the collar.

Figure 23:
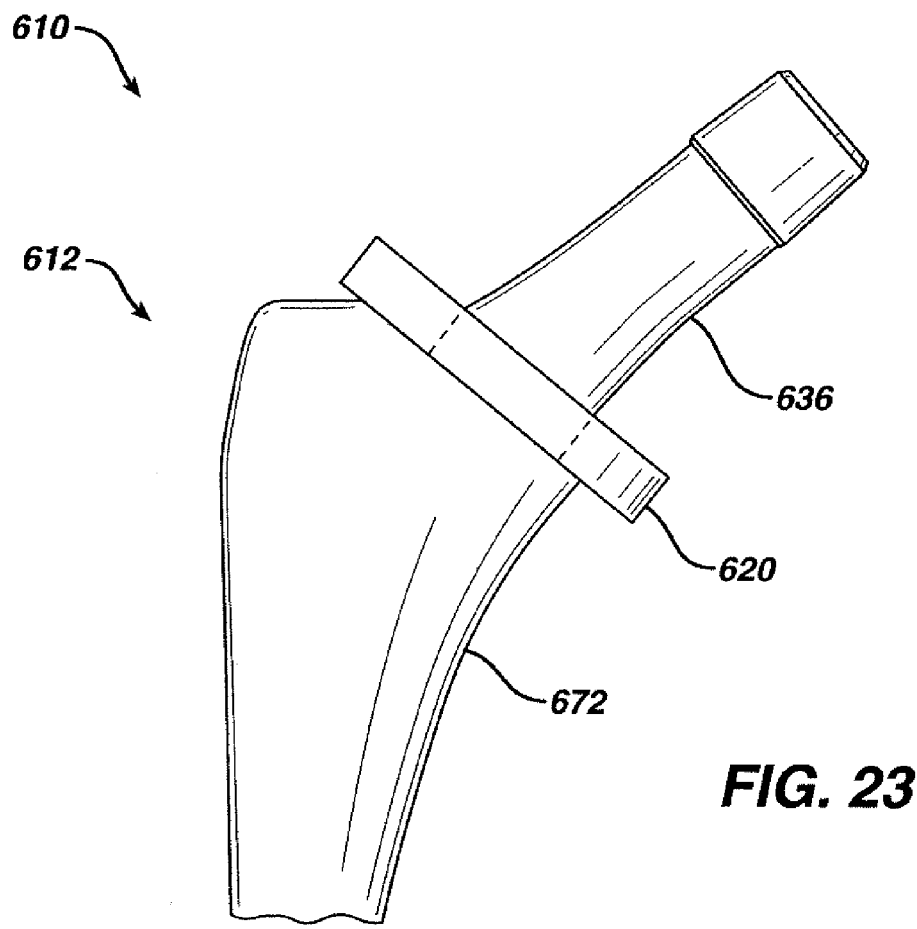
FIG. 23 is a partial plan view of a hip stem with a resorbable collar and no locking feature in accordance with a further embodiment of the present invention.

Referring now FIG. 23 another embodiment of the present invention is shown as prosthesis 610. Prosthesis 610 is similar to prosthesis 210 except that the prosthesis does not include a locking feature. The prosthesis 610 includes a stem 612 similar to stem 212 of the prosthesis 210 and includes a body 672 similar to body 272 of the prosthesis 210 and a neck 636 similar to neck 236 of the prosthesis 210. In addition to the stem 612 the prosthesis 610 includes a collar 620 which mates with the stem 612 to form the prosthesis 610. The collar 620 is similar to the collar 220 of the prosthesis 210 but does not include a locking feature. The stem 612 and the collar 220 are interconnected by an interference fit.

Referring now to FIGS. 24 through 30, prosthesis 710 according to the present invention is shown. The prosthesis 710 includes a stem 712 which has a body 772 and a neck 736. The neck 736 is removably connected to the body 772. Therefore, the stem 712 includes a body component 768 and a neck component 758. The prosthesis 710 also includes a collar 720 which restrainably positional between the body 772 and the neck 736.

The prosthesis according to the present invention may include a neck component 758 which is removably connected to a body component 768 in any suitable fashion. For example, the body component 768 and the neck component 758 may be connected by threadable connection, by bayonet connection or twist locking connection.

Figure 24:
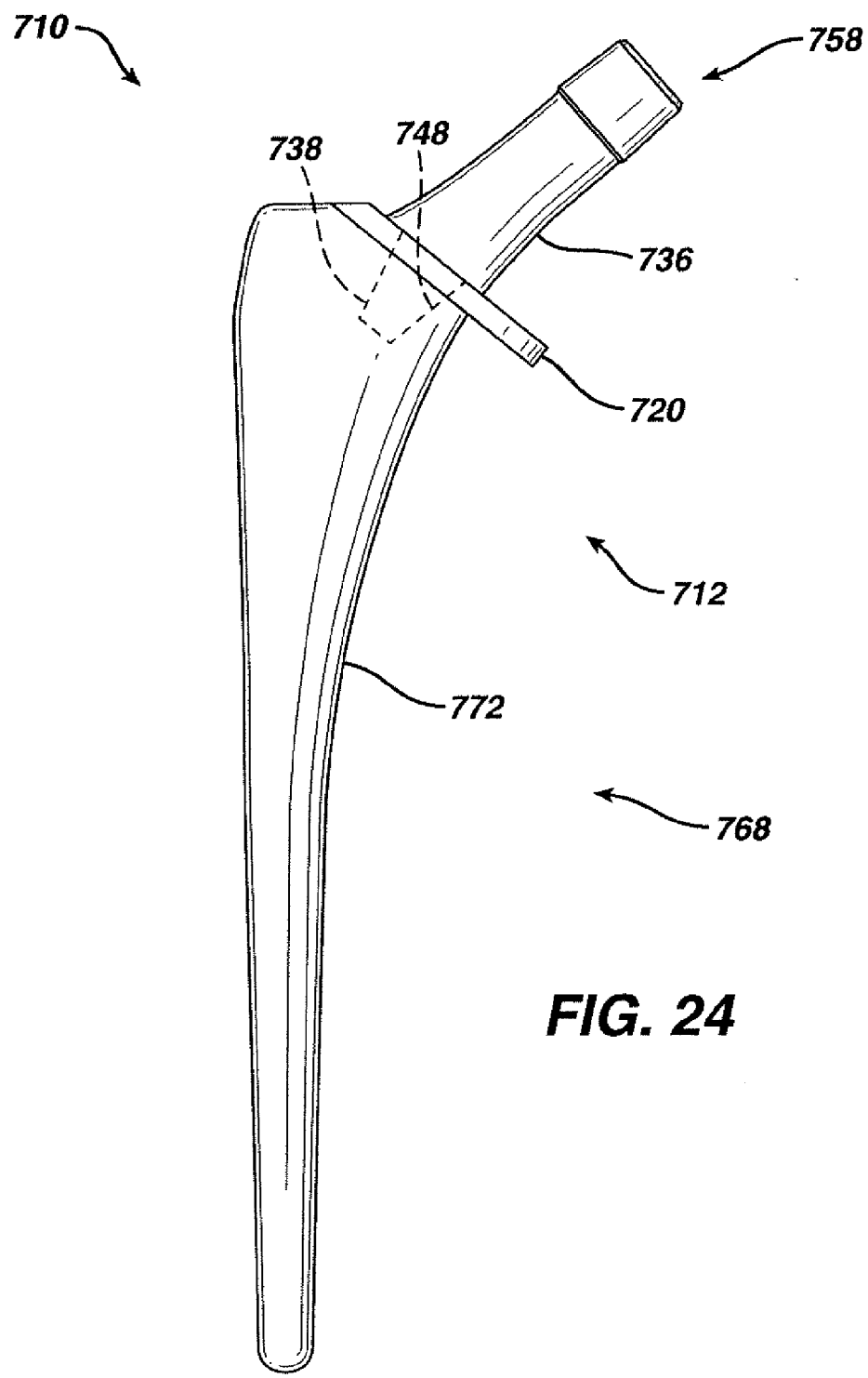
FIG. 24 is a plan view of the hip stem with a resorbable collar in accordance with a further embodiment of the present invention having interlocking neck and stem components with the resorbable collar installed.

As shown in FIG. 24, the prosthesis 710 may include a tapered male connector 738 in the neck component 758 which mates with a tapered female connection 748 located in the body component 768. It should be appreciated, however, that the tapered male connector 738 may, as well, be located in the body component 768 and the tapered female connector 748 may as likewise be located in the neck component 758.

The body component 768 includes a body 772 similar to the body 272 of the prosthesis 210 while the neck component 758 includes a neck 736 which is similar to the neck 236 of the prosthesis 210. The neck component 758 and the body component 768 are made of a material similar to the stem 12 of FIG. 1.

Figure 25:
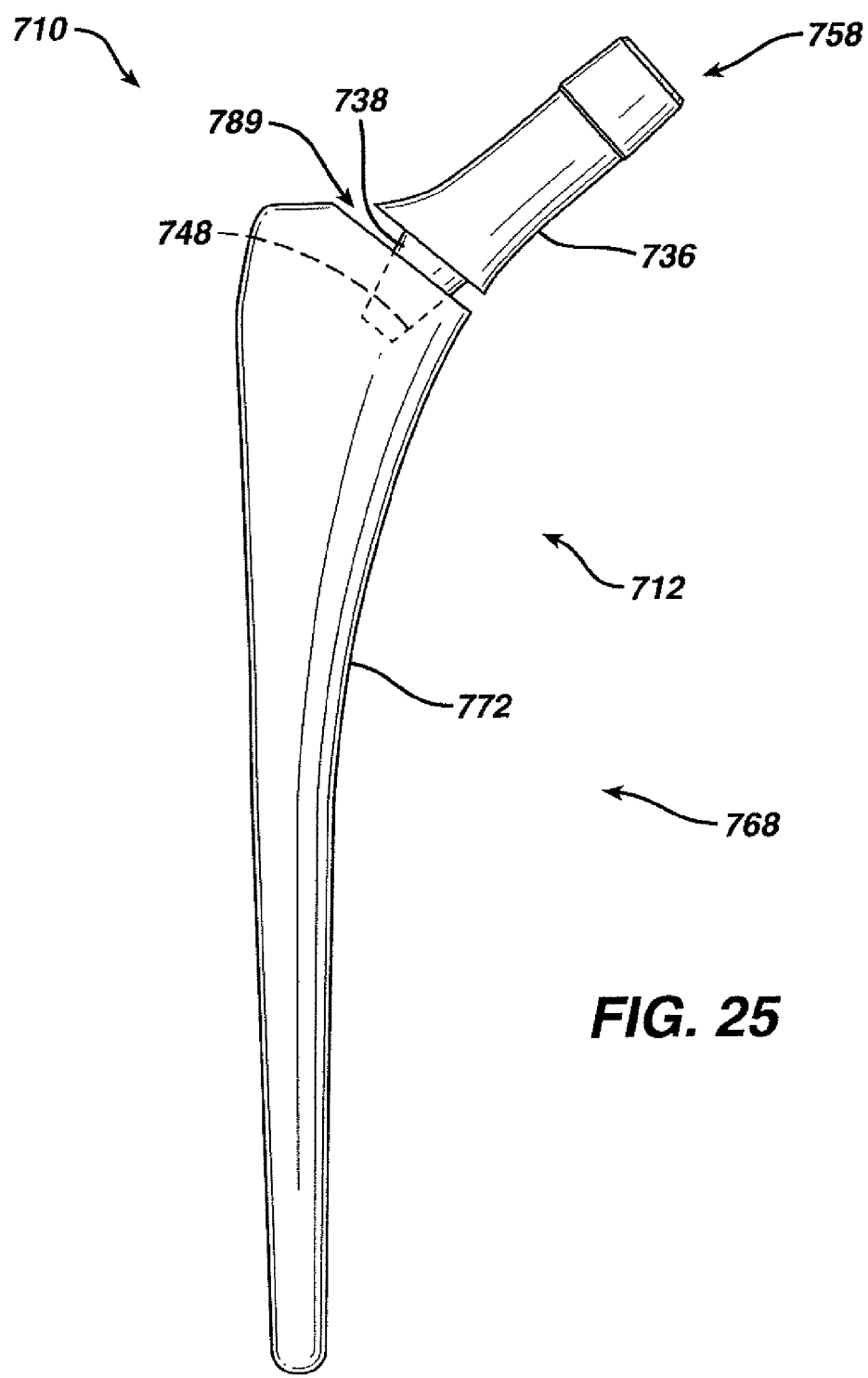
FIG. 25 is a plan view of the hip stem of FIG. 24 without the resorbable collar installed.

Referring now to FIG. 25, the prosthesis 710 is shown without the collar 720 in place. The body component 768 is shown in connection with the neck component 758. A gap or space 789 is shown between the parallel adjoining surfaces of the outer periphery of the neck component 758 and a body component 768. It is in this gap 789 that the collar 720 may be fitted. The tapered male connector 738 and the tapered female connector 748 are sized such that the gap 789 between the neck 736 and the body 772 is selected to provide for a secure positioning of the collar 720.

Figure 26:
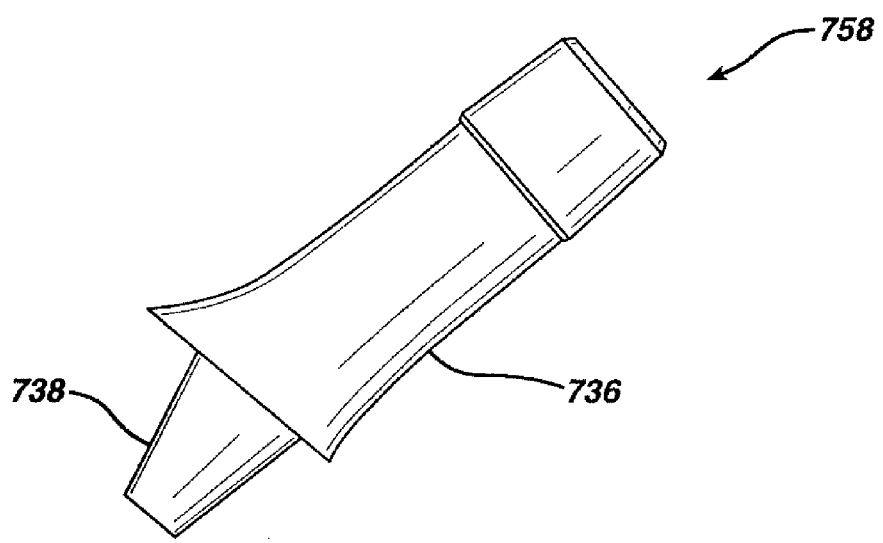
FIG. 26 is a plan view the neck portion of the hip stem in accordance with the embodiment of the present invention of FIG. 24.
Figure 27:
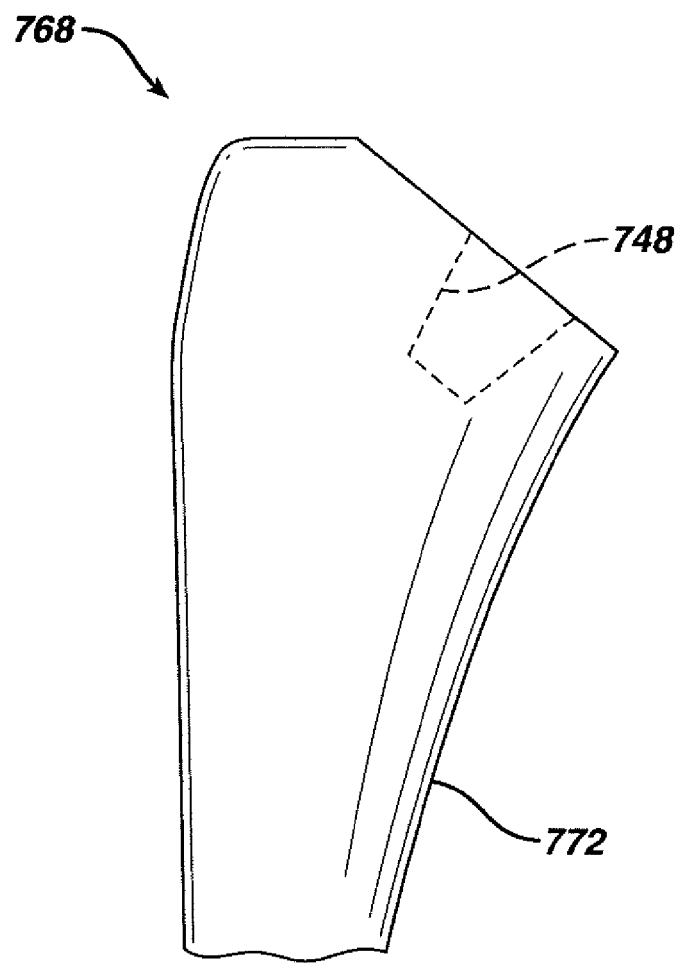
FIG. 27 is a plan view the body portion of the hip stem in accordance with the embodiment of the present invention of FIG. 24.

Referring now FIGS. 26 and 27, the neck component 758 and the body component 768 are shown as separate components. The neck component 758 includes the neck 736 to which the tapered male connector 738 is connected. The body component 768 includes the body 772 in which the tapered female connector 748 is formed.

Figure 28:
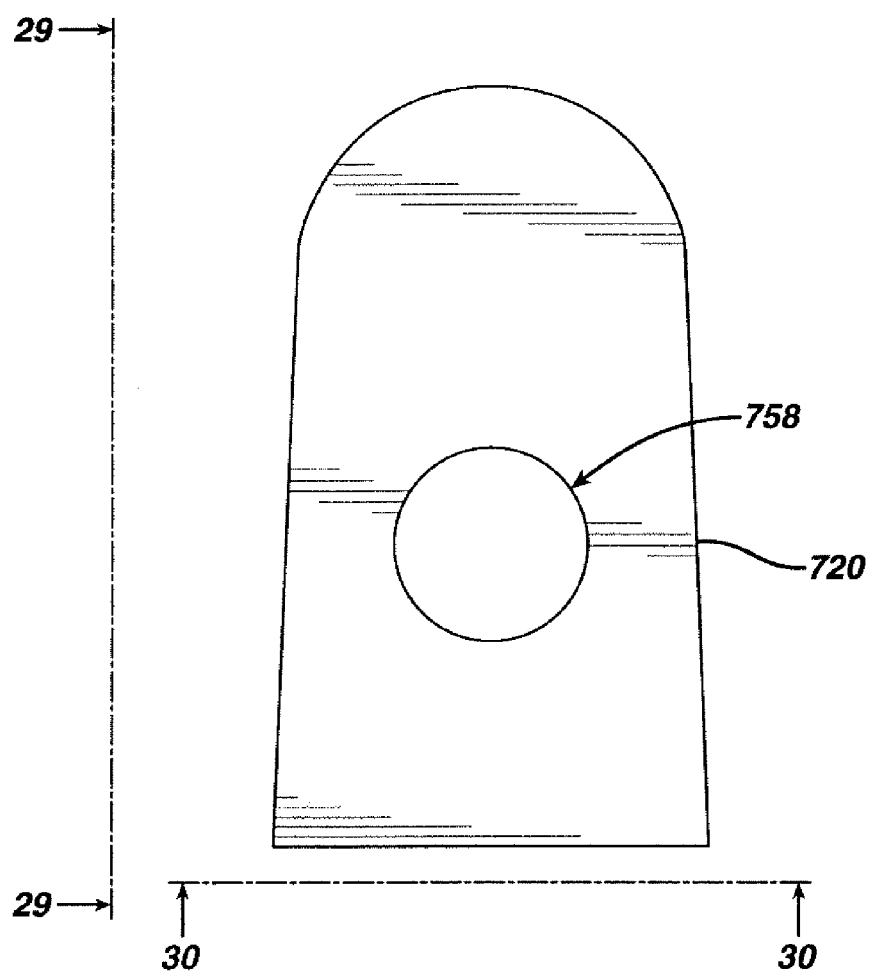
FIG. 28 is a plan view of a resorbable collar of the present invention for use in a hip stem in accordance with the embodiment of the present invention of FIG. 24.
Figure 29:
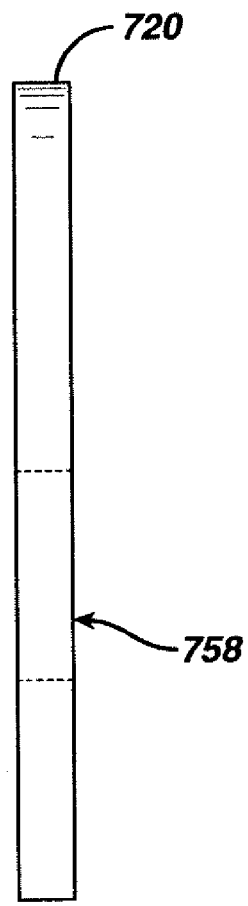
FIG. 29 is a view of the resorbable collar of FIG. 28 along the line 29—29 in the direction of the arrows.
Figure 30:
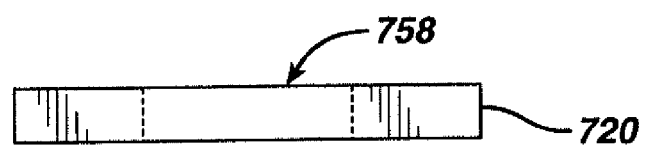
FIG. 30 is a view of the resorbable collar of FIG. 28 along the line 30—30 in the direction of the arrows.

Referring now to FIGS. 28 through 30, the collar 720 is shown. The collar 720 is similar to collar 20 of the prosthesis 10 and is preferably made of a resorbable material. Appropriate resorbable materials have been described herein. The collar 720 includes a hole 758 for permitting the tapered male connector 738 and the tapered female connector 748 to interconnect therebetween (see FIG. 25).

Figure 31:
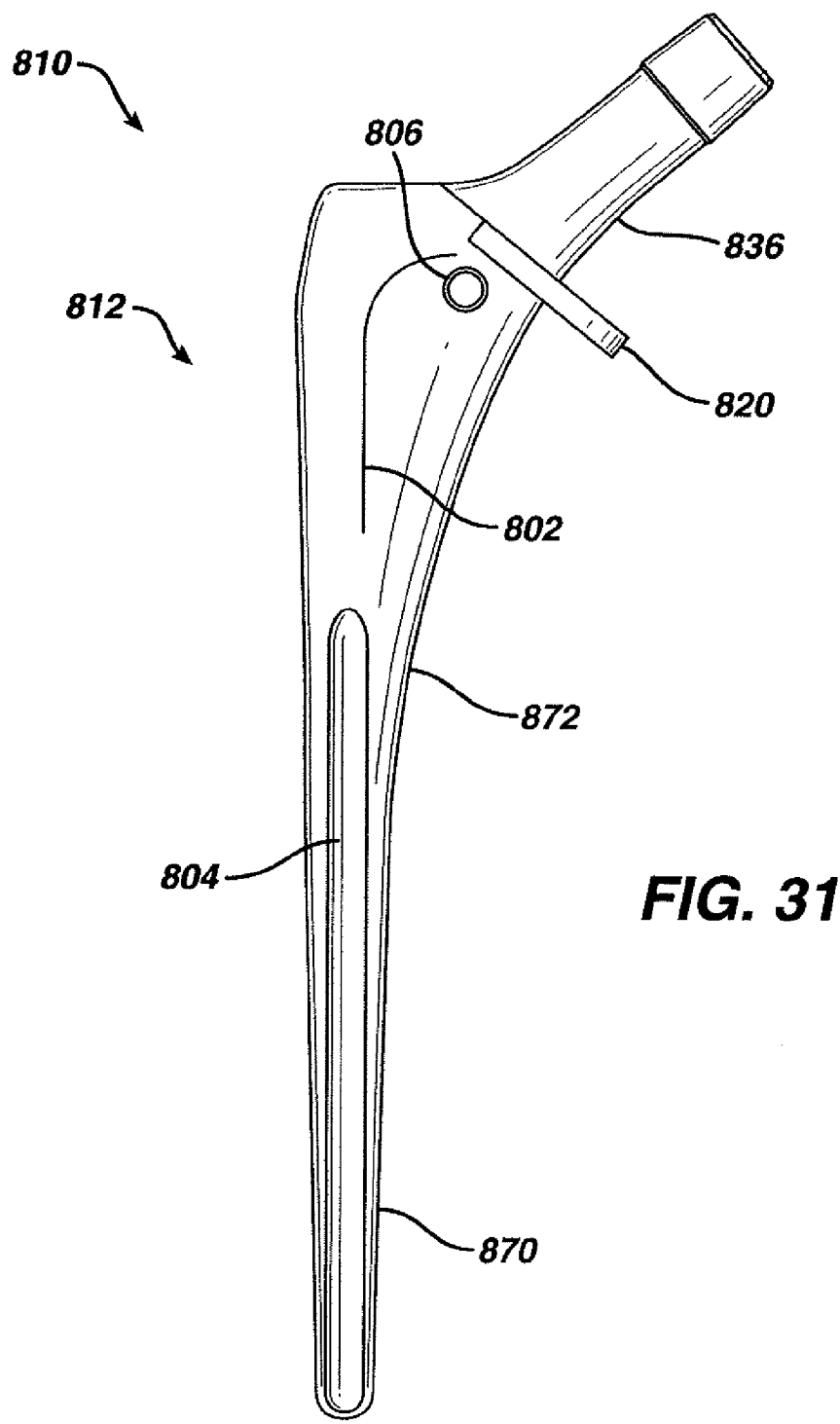
FIG. 31 is a plan view of another embodiment of a hip stem in accordance with the present invention having a stem with enhanced strength.

Referring now to FIG. 31 a partial view of another embodiment of the present invention utilizing the resorbable collar is shown as prosthesis 810 having stem 812. The stem 812 is shown with a shape to improve the strength/weight ratio of the stem. As shown in FIG. 31, body 872 of the stem 812 is similar to the body 72 of the stem 12 of FIG. 1, but includes a step 802 running vertically along the stem 872. The step 802 provides for extra strength for the stem 812.

The body 872 as shown in FIG. 31 further includes an external stem recess 804 running vertically along distal portion 870 of the body 872 of the stem 812. The stem recess 804 provides for additional stiffness of the stem 812. The body 872 may further include a manufacturing reference hole 806 for use in fixturing the stem 812 during manufacturing. A collar 820 is spaced between body 872 and neck 836.

Figure 32:
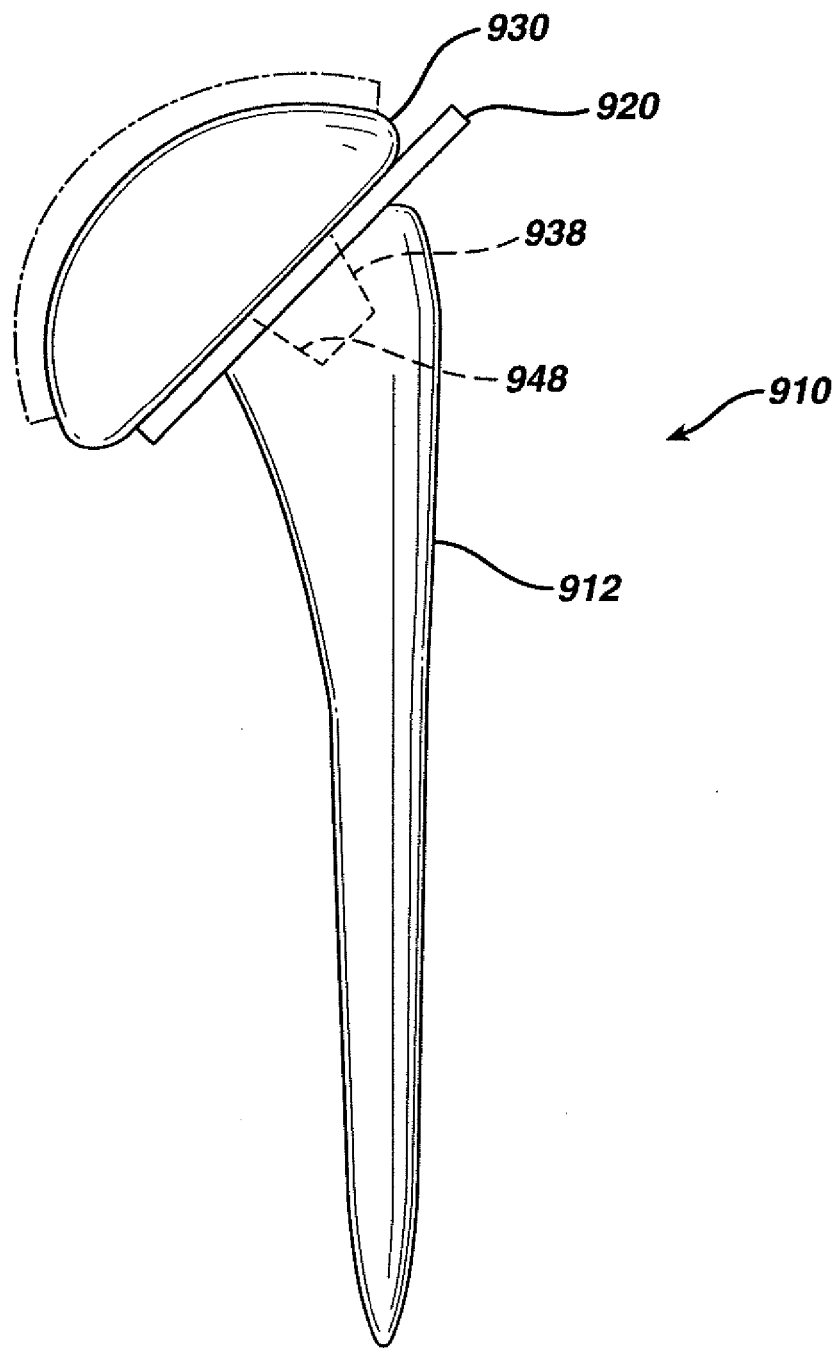
FIG. 32 is a plan view of a shoulder prosthesis with a resorbable collar and an interlocking stem and head in accordance with a further embodiment of the present invention with the head including a connection pin.

Referring now to FIG. 32 a plan view of another embodiment of the present invention utilizing the resorbable collar is shown as shoulder prosthesis 910. Shoulder prosthesis 910 includes a stem 912 having a tapered cavity 948 and a resorbable collar 920. The shoulder prosthesis 910 also includes a head 930 having a connection pin 938. The connection pin 938 in the head 930 interlocks with the tapered cavity 948 of the stem 912. The resorbable collar 920 is sandwiched between the stem 912 and the collar 920.

Figure 33:
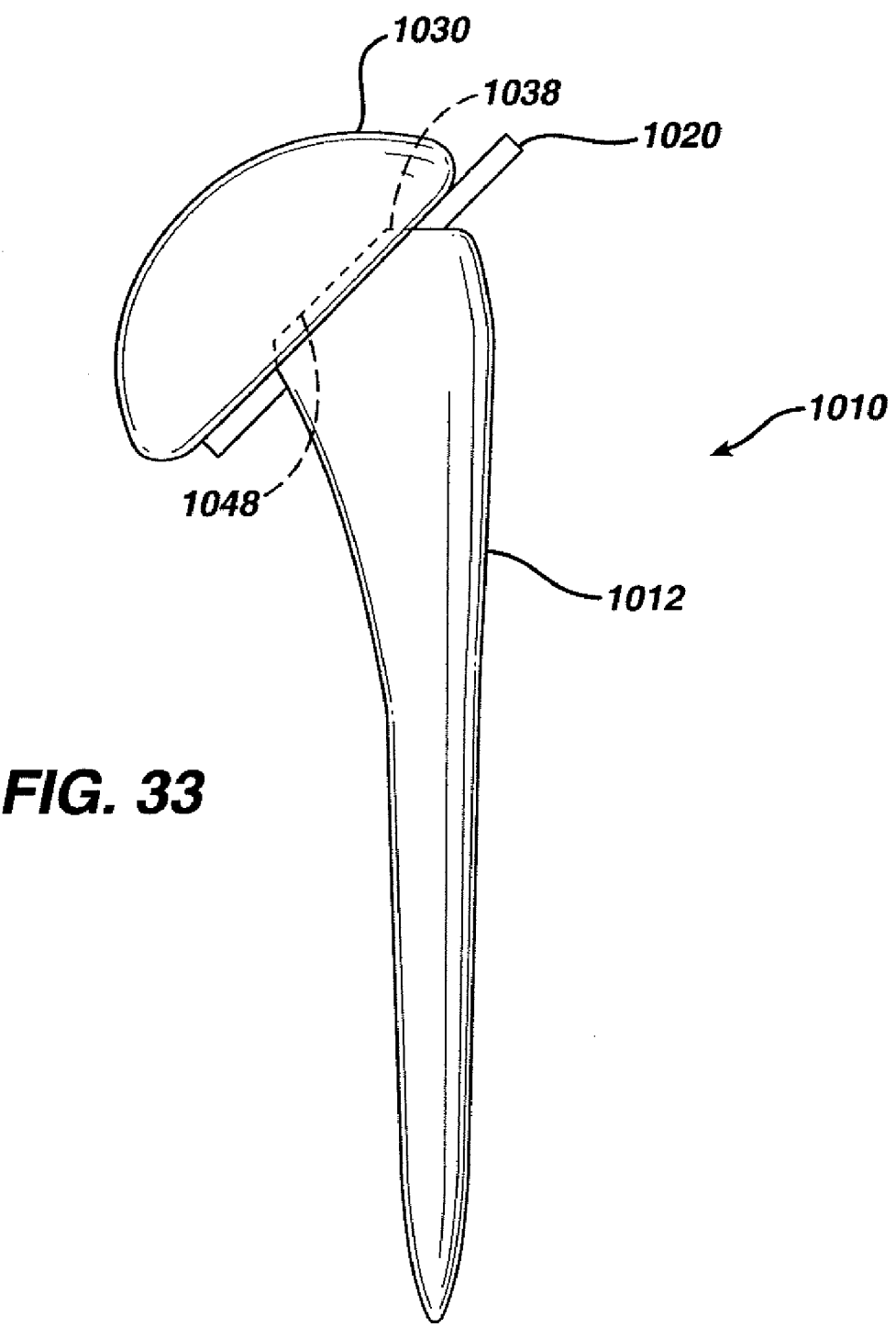
FIG. 33 is a plan view of a shoulder prosthesis with a resorbable collar and an interlocking stem and head in accordance with a further embodiment of the present invention with the stem including a connection pin.

Referring now to FIG. 33 a plan view of another embodiment of the present invention utilizing the resorbable collar is shown as shoulder prosthesis 1010. Shoulder prosthesis 1010 includes a stem 1012 having a connection pin 1038 and a resorbable collar 1020. The shoulder prosthesis 1010 also includes a head 1030 having tapered cavity 1048. The connection pin 1038 in the stem 1012 interlocks with the tapered cavity 1048 of the head 1030. The resorbable collar 1020 is sandwiched between the stem 1012 and the collar 1020.

It should be appreciated that the stem or collar of the prosthesis of the present invention may be adapted to provide for a selectable plurality of implantable positions of the collar with respect to the stem. For example, and referring now to FIG. 34, a prosthesis 1110 is shown which provides for a plurality of selectable implantable positions for the collar with respect to the stem.

The prosthesis 1110 is similar to prosthesis 10 of FIG. 1 and includes a stem 1112 which is generally similar to stem 12 of prosthesis 10 of FIG. 1. The prosthesis 1110 further includes a head 1130 which is fittable to stem 1112. The head 1130 is similar to head 30 of prosthesis 10 of FIG. 1. The prosthesis 1110 further includes a cup 1146 which is fitted to acetabulum 54. The cup 1146 is similar to cup 46 of the prosthesis 10 of FIG. 1 and may, as the prosthesis 10 of FIG. 1, include a liner 1160 similar to liner 60 of the prosthesis 10 of FIG. 1.

Figure 34:
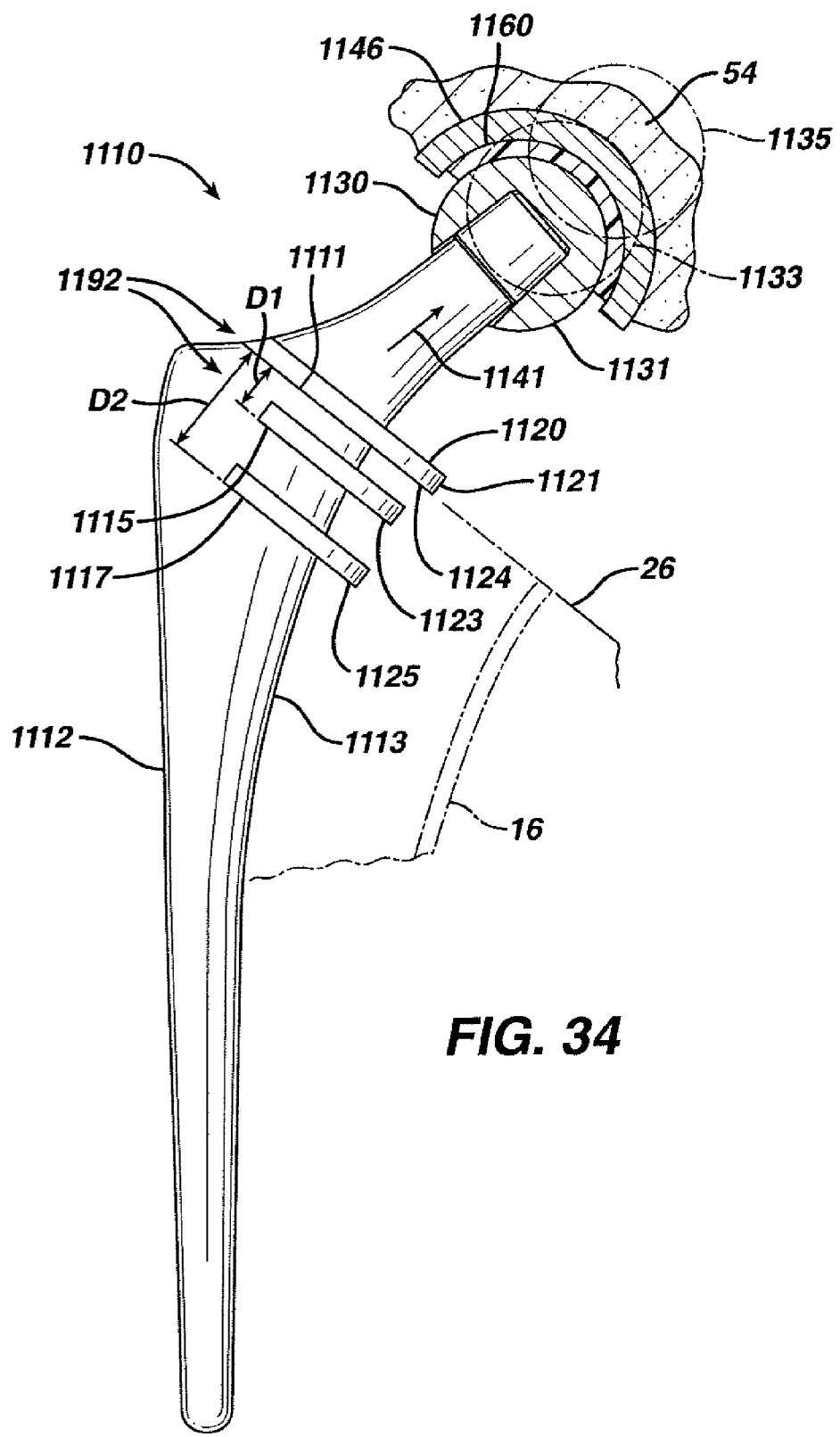
FIG. 34 is a plan view of a hip prosthesis with a plurality of spaced apart grooves along the prosthesis stem and a resorbable collar which may be selectively placed in one of the grooves so that a common stem may be utilized in patients with varied anatomies in accordance with a further embodiment of the present invention.

As shown in FIG. 34, the stem 1112 may include grooves 1192 with each of the grooves 1192 being similar to groove 92 of the stem 12 (see FIG. 3).

As shown in FIG. 34, the prosthesis 1110 may include among the grooves 1192 a first groove 1111 which is shown in position against resected surface 26 of the long bone 16. As shown in FIG. 34, the first groove 1111 is shown generally perpendicular to medial surface 1113 of the stem 1112. The collar 1120 preferably matingly fits within the first groove 1110 to provide support for the stem 1112 in accordance to the present invention.

In addition to the first groove 1111, the stem 1112 may include a second groove 1115 which is spaced from first groove 1111. The second groove 1115 is similar in size and configuration with the first groove 1111. The second groove 1115 may be parallel to the first groove 1111 or may, like first groove 1111, be generally perpendicular to medial surface 1113 of the stem 1112.

In addition to the first groove 1111 and the second groove 1115, the prosthesis 1110 may include a third groove 1117 positioned on stem 1112. The third groove 1117 may be parallel and spaced from first groove 1111 and second groove 1115 or may be perpendicular to the medial surface 1113 of the stem 1112. Similar to the first groove 1111 and the second groove 1115, the third groove 1117 is provided with the size and shape for secure cooperation with the collar 1120.

As shown in FIG. 34, when the collar 1120 is in first groove 1111, the collar 1120 is in a first collar position 1121. At first collar position 1121, the head 1130 is in first head position 1131 as shown in solid. Similarly, when the collar 1120 is in second groove 1115 as shown in phantom, the collar 1120 is in second collar position 1123 and correspondingly the head 1130 is in second head position 1133 as the stem 1112 is moved in the direction of arrow 1141 to provide for the collar 1120 to rest against resected surface 26 when the collar 1120 is in the second groove 1115.

Similarly, when the collar 1120 is positioned in third groove 1117, the collar is in third collar position 1125, as shown in phantom, and the stem, after moving in the direction of arrow 1141, results in the head 1130 being in third head position 1135 as shown in phantom. Thus, it can be shown that by utilizing the prosthesis 1110, a common stem 1112 and collar 1120 may be utilized to provide for a variety of head positions utilizing the same prosthesis 1110. Thus, the prosthesis 1110 may be utilized for patients with a variety of anatomical needs.

Figure 35:
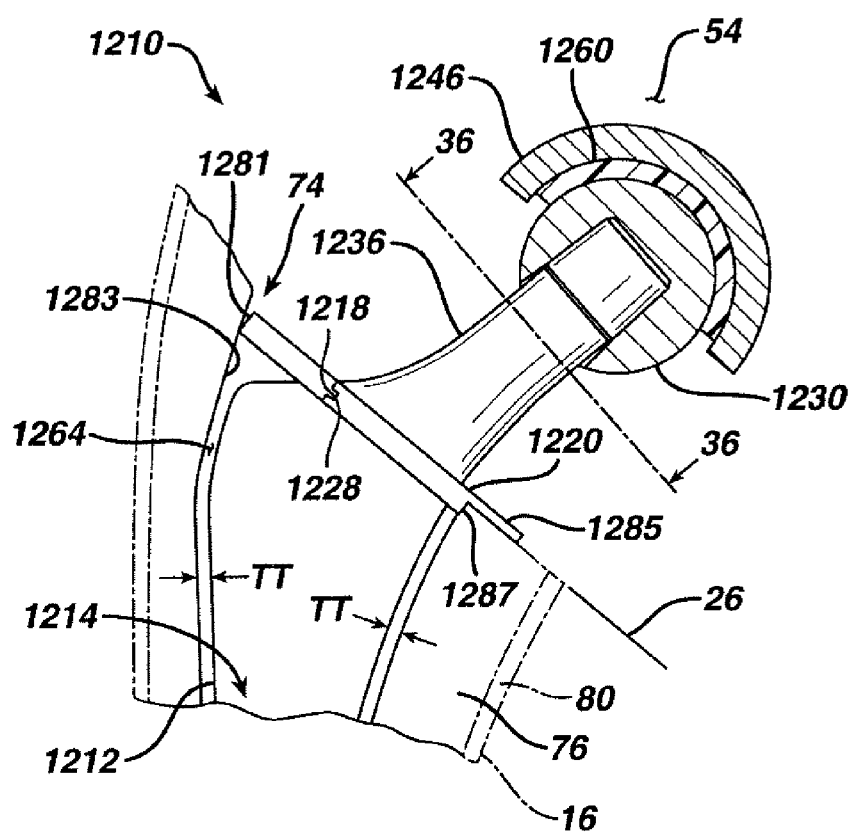
FIG. 35 is a plan view of a hip prosthesis with a resorbable collar including an embodiment of a resorbable collar which may be also used as a proximal stem centralizing device which may installed onto the stem along the neck in accordance with a further embodiment of the present invention.
Figure 36:
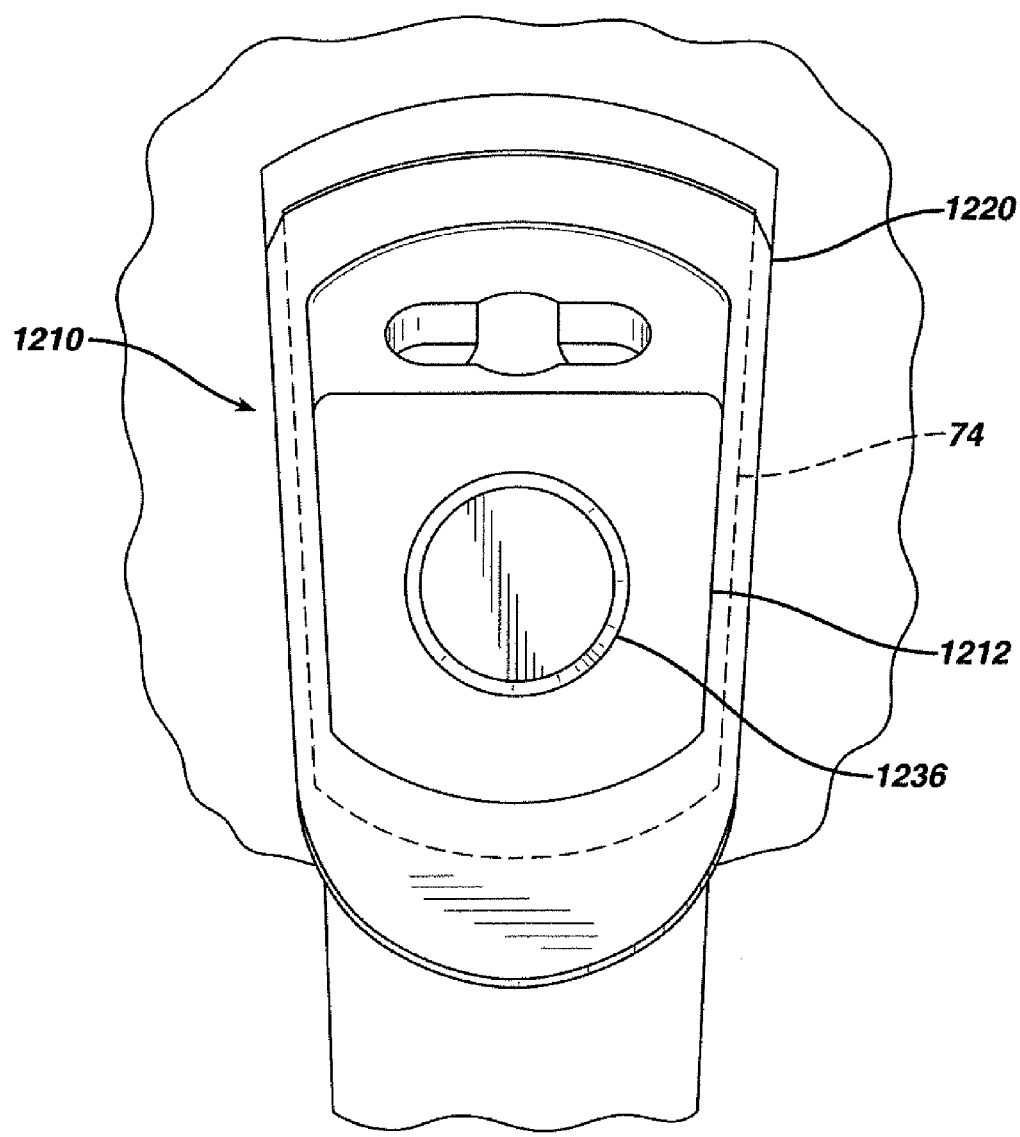
FIG. 36 is a view along the lines 36—36 in the direction of the arrows of the hip prosthesis of FIG. 35.

Referring now to FIGS. 35 and 36, another embodiment of the present invention is shown as prosthesis 1210. Prosthesis 1210 provides an additional advantage of providing for proximal centralization of the prosthesis within the broached cavity of the medullary canal. Centralization of the prosthesis 1210 within the broached cavity provides for uniform cement mantle around the prosthesis which provides for optimum support for the prosthesis within the patient.

The prosthesis 1210, as shown in FIGS. 35 and 36, is similar to the prosthesis 210 of FIGS. 11 to 20. The prosthesis 1210 includes a stem 1212 to which a head 1230 is attached. The head 1230 rotates about cup 1246 secured to acetabulum 54. As shown in FIGS. 35 and 36, the prosthesis 1210 may include a liner 1260 positioned between the cup 1246 and the head 1230. The head 1230, the cup 1246, and the liner 1260 of the prosthesis 1210 may be similar to the head 230, the cup 246 and the liner 260 of the prosthesis 210 of FIGS. 11 to 20.

The stem 1212 of the prosthesis 1210 is similar to the stem 212 of the prosthesis 210 of FIGS. 11 to 20 and includes a dimple 1218 for receiving collar 1220. The collar 1220 includes a bump 1228 which mates with the dimple 1218 of the neck 1236 of the stem 1212. The dimple 1218 and the bump 1228 serve to provide support for the stem 1212 during installation of the stem 1212 into the cavity 74 formed in medullary canal 14 of the patient.

The collar 1220 is somewhat different than collar 220 of the prosthesis 210 of FIGS. 11 to 20 in that the collar 1220 further serves to centralize the stem 1212 within the cavity 74. In order that the collar 1220 may be utilized to centralize the stem 1212, the collar 1220 includes a collar outer periphery 1281 which is designed to matingly fit with cavity periphery 1283. A portion of collar 1220 may rest on resected surface 26 of the long bone 16. The collar 1220 may rest on the cancellous bone 76 or may also rest on cortical bone 80. To provide a centralizing feature in the collar 1220 adjacent the portion of the collar 1220 that rests upon resected surface 26, the collar 1220 may include a lip 1285 which forms a collar inner-periphery 1287. The collar inner-periphery 1287 matingly fits with cavity periphery 1283 to assist in centralizing the collar 1220.

By placing the collar 1220 onto neck 1236 of the stem 1212, the collar 1220 centralizes the stem 1212 within cavity 74. The stem 1212 thus is an equal distance preferably of TT from cavity periphery 1283 formed by cavity 74. The space between the cavity periphery 1283 and the stem 1212 is filled with PMMA and forms cement mantle 1264 between the cancellous bone 76 and the stem 1212. The thickness of the cement mantle 1264 thus is uniformly a thickness of TT. By providing a uniform thickness of the cement mantle 1264, the implantation of the prosthesis 1210 may be optimized.

Figure 37:
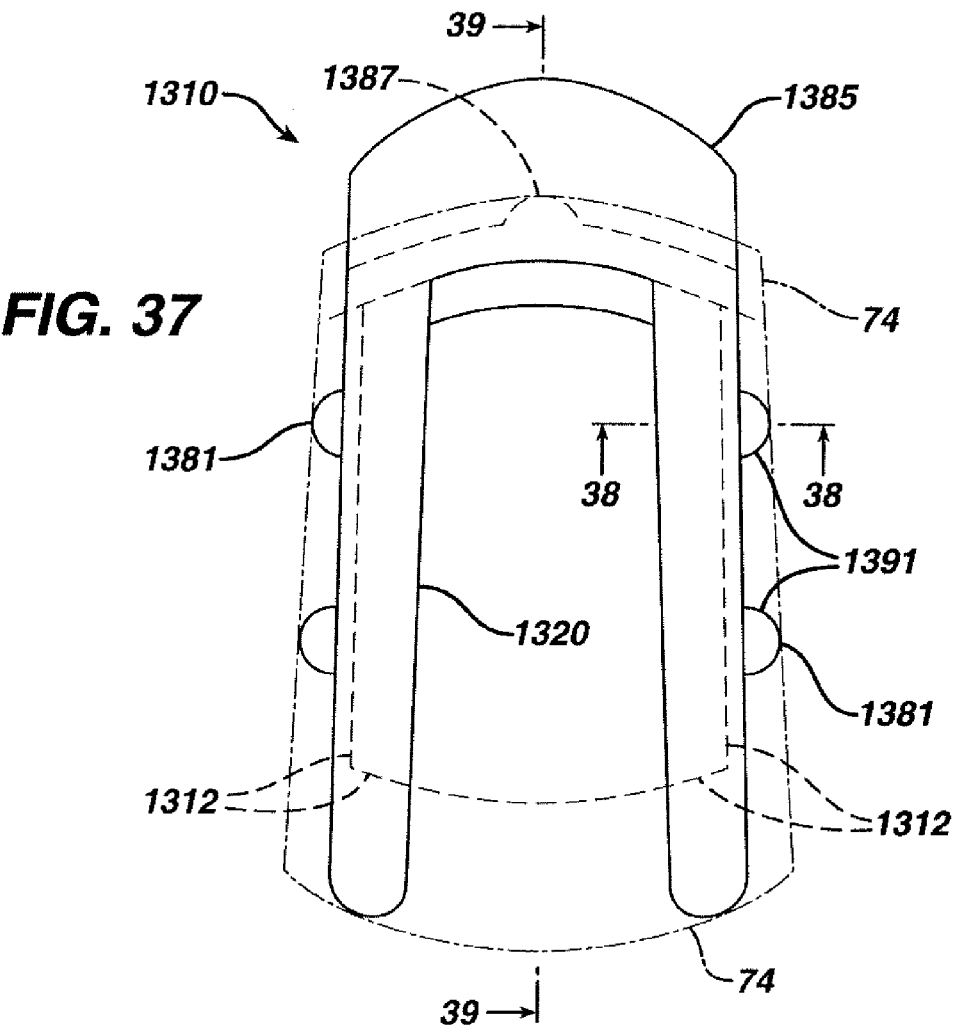
FIG. 37 is a top view of a resorbable collar for a hip prosthesis showing a portion of the hip prosthesis in phantom showing an embodiment of a resorbable collar which may also be used as a proximal stem centralizing device which may installed into grooves in the stem according to a further embodiment of the present invention.
Figure 38:
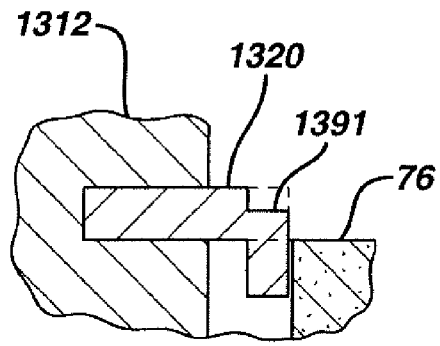
FIG. 38 is a partial cross sectional view along the lines 38—38 in the direction of the arrows of the hip prosthesis of FIG. 37.
Figure 39:
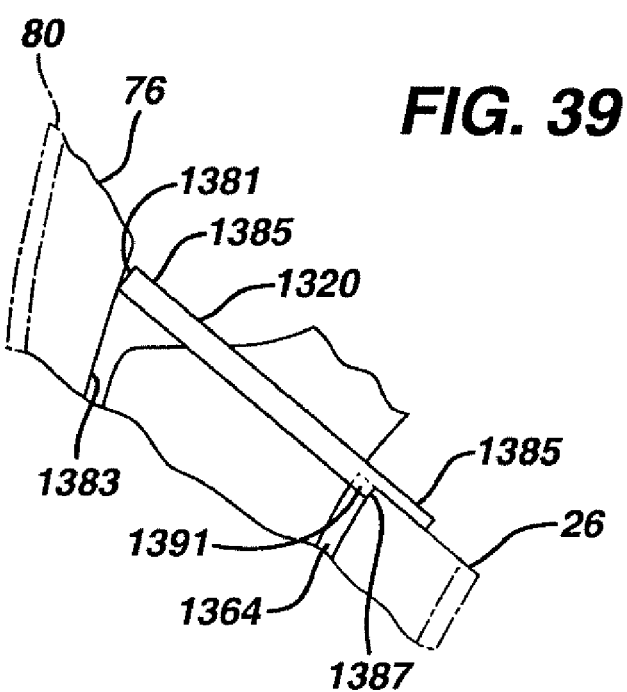
FIG. 39 is a partial cross sectional view along the lines 39—39 in the direction of the arrows of the hip prosthesis of FIG. 37.

Referring now to FIGS. 37, 38 and 39, another embodiment of the present invention is shown as prosthesis 1310. Prosthesis 1310, like prosthesis 1210 of FIGS. 35 and 36, provides for proximal centralization of the stem by utilizing a centralizing collar. The prosthesis 1310 is similar to prosthesis 10 of FIGS. 1 through 10 and includes a stem 1310 (shown in phantom) similar to stem 12 of FIGS. 1 through 10.

The prosthesis 1310 further includes a collar 1320 similar to collar 20 of FIGS. 1 through 10 except that the collar 1320 has been adapted to centralize the stem 1312 within the cavity 74 of the prosthesis 1310. The collar 1320 thus includes a collar outer-periphery 1381 which contacts cavity periphery 1383 formed by cavity 74 in the cancellous bone 76 of the long bone 16.

The prosthesis 1310 may further include a lip 1385 which provides support for the prosthesis 1310 by having the lip 1385 rest against resected surface 26 of the cancellous bone 76. The lip 1385 forms collar inner-periphery 1387. The collar inner-periphery 1387 further centralizes the collar 1320 within the cavity 74. It should be appreciated that the collar outer-periphery 1381 and the collar inner-periphery 1387 may generally correspond in shape to the cavity 74 or the stem 1312 or may, as shown in FIGS. 37, 38 and 39, include arcuate protrusions 1391. The arcuate protrusions 1391 may be used to contact the cavity periphery 1383 of the cavity 74.

By providing a highly polished tapered femoral prosthesis that is assembled with a collar made of a resorbable material, a process may be provided that utilizes a collar to improve cement pressurization.

By providing a highly polished tapered female prosthesis that is assembled with a resorbable collar the cement stress distribution may be optimized by providing for a proper positioning of the prosthesis and by permitting control subsidence of the prosthesis.

By providing a highly polished tapered femoral prosthesis with a resorbable collar a consistent cement mantle thickness may be provided by utilizing the collar to properly position the prosthesis.

By providing a highly polished tapered femoral prosthesis with a resorbable collar, the generation of cement debris may be minimized. By providing a highly polished tapered femoral prosthesis with a resorbable collar, initial and final stem position may be optimized by utilizing the collar to properly position the prosthesis against the resection line of the femur.

It should be appreciated that while the figures of the present invention show the use of a prosthesis with a resorbable collar in the form of a femur hip stem, it should be appreciated that the invention may be equally suitable for a shoulder prosthesis. A resorbable collar may be desirable to position a shoulder stem into the humerus and to locate the shoulder against the resected humerus.

It should also be appreciated that a resorbable collar may be desirable in other long bones for example, in an ulna or a tibia.

Although the present invention and its advantages have been described in detail, it should be understood that various changes, substitutions, and alterations can be made therein without departing from the spirit and scope of the present invention as defined by the appended claims.

What is claimed is:

1. A method for providing total hip arthroplasty comprising:
    resecting a long bone to form a resected face thereof,
    opening a medullary canal of the long bone,
    inserting cement into the canal,
    providing a stem,
    placing a resorbable collar in cooperation with the stem,
    implanting the prosthesis at least partially within the medullary canal,
    positioning the collar on the resected face of the long bone,
    resorbing the collar, and
    subsiding the stem in a controlled manner into the cement mantle.

2. The method for providing total hip arthroplasty of claim 1, further including the steps of:
    providing at least one of the stem and the collar with a selectable plurality of implantable positions of the collar with respect to the stem, and
    selecting one of the plurality of implantable positions of the collar.

3. The method for providing total hip arthroplasty of claim 1, further including the steps of:
    providing a collar which is adapted to centralize the stem within the medullary canal, and
    utilizing the collar to centralize the stem.

* * * * *